(12) United States Patent
Demirci et al.

(10) Patent No.: US 10,094,759 B1
(45) Date of Patent: Oct. 9, 2018

(54) IMAGING DEVICE FOR MEASURING SPERM MOTILITY

(71) Applicant: Hillel LLC, Stanford, CA (US)

(72) Inventors: Utkan Demirci, Stanford, CA (US); Selcuk Kilinc, Izmir (TR)

(73) Assignee: HILLEL LLC, Stanford, CA (US)

( * ) Notice: Subject to any disclaimer, the term of this patent is extended or adjusted under 35 U.S.C. 154(b) by 0 days.

(21) Appl. No.: 15/853,124

(22) Filed: Dec. 22, 2017

(51) Int. Cl.
| | |
|---|---|
| *H04N 7/18* | (2006.01) |
| *G01N 23/04* | (2018.01) |
| *G01N 15/14* | (2006.01) |
| *H04N 5/357* | (2011.01) |
| *B01L 3/00* | (2006.01) |
| *G01N 15/00* | (2006.01) |
| *G01N 15/10* | (2006.01) |

(52) U.S. Cl.
CPC ......... *G01N 15/1431* (2013.01); *B01L 3/508* (2013.01); *G01N 15/1434* (2013.01); *H04N 5/357* (2013.01); *B01L 2200/025* (2013.01); *B01L 2300/04* (2013.01); *B01L 2300/047* (2013.01); *B01L 2300/0809* (2013.01); *B01L 2300/0832* (2013.01); *G01N 2015/0065* (2013.01); *G01N 2015/1006* (2013.01); *G01N 2015/1477* (2013.01)

(58) Field of Classification Search
CPC ............ G01N 15/1431; G01N 15/1434; B01L 3/508; H04N 5/357
USPC .......................................................... 348/79
See application file for complete search history.

(56) References Cited

U.S. PATENT DOCUMENTS

| | | | |
|---|---|---|---|
| 2009/0072171 A1* | 3/2009 | So ...................... | G06K 9/00127 250/584 |
| 2013/0194410 A1 | 8/2013 | Topman et al. | |
| 2014/0152801 A1* | 6/2014 | Fine .................. | G02B 21/0008 348/79 |
| 2014/0254004 A1 | 9/2014 | Wooder et al. | |

OTHER PUBLICATIONS

Amann, et al., Computer-Assisted Sperm Analysis (CASA): Capabilities and Potential Developments, Theriogenology, 2014, 81:5-17.
Di Caprio, et al., Holographic Imaging of Unlabelled Sperm Cells for Semen Analysis: A Review, J. Biophotonics, 2015, 8(10):779-789.

* cited by examiner

*Primary Examiner* — Hee-Yong Kim
(74) *Attorney, Agent, or Firm* — Wilson Sonsini Goodrich & Rosati

(57) ABSTRACT

Disclosed herein are imaging-based devices and systems for measuring sperm motility in samples of human or animal origin. The disclosed devices and systems have particular applicability in the fields of agricultural and clinical diagnostics, as well as in vitro fertilization.

30 Claims, 28 Drawing Sheets

Detail B
Scale 2:1

SEMEN ANALYSIS REPORT

SpermCell

Test Time: 10/11/2017 12:35

| Reference | 1234567890 |
|---|---|
| Patient Name, Surname | Ahmet Sanli |
| Birth Date | 21.09.1978 |

| Collection Date | 10/11/2017 | Appearance | Normal |
|---|---|---|---|
| Volume (mL) | 2,5 | | |
| Abstinence Days | 3 | | |
| Collection Method | Laboratory | | |
| Viscosity | Normal | | |

Concentration

| 17.000.000 Sperm/mL | 42.500.000 Sperm/Ejac | 2,5 mL | Dilution 1:0 |
|---|---|---|---|

Motility (WHO4)

| | Concentration | % | Conc / Ejac | Reference |
|---|---|---|---|---|
| Total Motile Sperm Count | 13.000.000 | 76,47 | 0,30 | |
| Progressive Motility (Type A) | 6.500.000 | 50 | | (> % 25) |
| Curvilinear Motility (Type B) | 3.250.000 | 25 | | |
| Non Progressive (Type C) | 3.250.000 | 1,47 | | |
| Immotile (Type D) | 4.000.000 | 23,53 | | |

Velocity (WHO4)

| | Minimum | Maximum | Average | Reference |
|---|---|---|---|---|
| Curvilinear Velocity - VCL (µm/s) | 0,0 | 50,0 | 32,0 | |
| Average Path Velocity - VAP (µm/s) | 0,0 | 50,0 | 29,3 | |
| Straight Line Velocity - VSL (µm/s) | 0,0 | 50,0 | 29,5 | |
| Progression (µm) | 0,0 | 160,0 | 79,5 | |

FIG. 25

SpermCell CASA Software Validation

| Patient Information | Trial No. | Makler Counting Chamber | | |
|---|---|---|---|---|
| | | Patient Age | Sperm Concentration | % Mobility |
| 971579 | 1 | | 69,000,000 | 50% |
| | | | 64,000,000 | |
| | | | 79,000,000 | |
| | 2 | | 53,000,000 | 62% |
| | | | 54,000,000 | |
| | | | 40,000,000 | |
| | 3 | | 60,000,000 | 40% |
| | | | 63,000,000 | |
| | | | 52,000,000 | |
| Average | | | 59,333,333 | 50.6% |

FIG. 28

IMAGING DEVICE FOR MEASURING SPERM MOTILITY

BACKGROUND

The disclosed invention relates to the field of imaging and analyzing the motion of motile organisms in general (e.g., cells, gametes, or single-celled organisms), and in particular to the field of imaging and analyzing sperm motility.

Analysis of sperm motility, i.e., the measurement of their ability to move properly, for the assessment of male reproductive health and the likelihood of successful outcomes in natural or artificial insemination has become a widely used tool in both agricultural and clinical diagnostics (R. Amann and D. Waberski (2014), "Computer-Assisted Sperm Analysis (CASA): Capabilities and Potential Developments", Theriogenology 81:5-17; G. Di Caprio, et al. (2015), "Holographic Imaging of Unlabelled Sperm Cells for Semen Analysis: A Review", J. Biophotonics 8(10):779-789). In humans, sperm concentration, morphology and motility measurements conducted as part of a semen analysis are used to assess male fertility. In agricultural settings, animal semen analysis is used in assessing the quality of semen samples, including previously frozen semen samples, for artificial insemination at stud farms and farm animal breeding facilities.

The rapid growth in the use of artificial insemination in the cattle industry starting in the late 1940s and early 1950s led to a need for objective methods to evaluate sperm quality (R. Amann and D. Waberski (2014)). Early approaches were based on microscopy-based observation, which through subsequent advancements in film-based or electronic imaging technologies, digital computing, and image processing software have led to the development of modern computer-assisted sperm analysis (CASA) systems. In a typical commercially-available CASA system, phase contrast microscope images of sperm (confined to motion in two-dimensions within a shallow sample chamber) are acquired using an image sensor which converts the images to digital data (at rates of 50 to 60 frames per second) that may be stored and manipulated using a computer and appropriate software. Image processing software algorithms perform edge detection and object (sperm cell) identification within each image frame, centroid calculations for each sperm cell detected within the field-of-view, tracking of centroids from one image frame to the next to identify trajectories or paths of motion, and estimation of the velocity or other motion parameters for each sperm cell detected within the field-of-view. CASA systems may provide a variety of in-plane motility data (for each individual sperm cell or for the population) such as straight-line velocities, curvilinear velocities, percentage of sperm exhibiting a velocity greater than a specified threshold value, and degree of linearity of motion (R. Amann and D. Waberski (2014); G. Di Caprio, et al. (2015)). Some CASA systems also provide sperm morphology analysis capabilities. A number of experimental and instrument design parameters may affect the accuracy and precision of CASA system output data, including sperm type, the type of extender or medium used for sample preparation, specimen chamber dimensions (in particular, chamber depth), the intensity of illumination, imaging hardware and software, instrument settings, technician training and skill level, etc.

The importance of CASA system data for assessing the product quality of semen marketed for artificial insemination of cattle, horses, or pigs is increasing (Amann & Waberski (2014)). Because most commercially-available CASA systems are quite large and expensive, there is a need for a field-use, portable CASA system capable of measuring the motion and/or morphology attributes of individual sperm. Such a system would be beneficial to veterinarians treating farm animal and race horse reproductive issues, veterinarians and technicians working at stud farms and farm animal breeding facilities that utilize artificial insemination techniques, and to physicians treating male reproductive problems in rural areas or smaller urban centers.

SUMMARY

Disclosed herein are devices for imaging a sample, the devices comprising: a) a substantially planar first component, wherein the first component comprises an alignment feature and a sample chamber configured to hold the sample to be imaged, and wherein at least one surface of the sample chamber is optically transparent; and b) a removable, substantially planar second component that forms a lid for the sample chamber and that comprises a micro lens, wherein the micro lens is optically aligned with the sample chamber and contacts the sample or is placed in close proximity to the sample when the removable second component is positioned in the alignment feature.

In some embodiments, the first component comprises two or more sample chambers. In some embodiments, the micro lens is a ball lens, a cylindrical lens, or a rectangular lens. In some embodiments, the micro lens is a ball lens and has a diameter of between about 0.5 mm and about 2 mm. In some embodiments, the micro lens is fabricated from H-ZLaF71, LaSFN9, or S-LAH79. In some embodiments, an effective focal length of the micro lens is between about 0.25 mm and about 1 mm. In some embodiments, an effective focal length of the micro lens is about 0.82 mm. In some embodiments, a back focal length of the micro lens is between about 0.01 mm to about 0.1 mm. In some embodiments, a back focal length of the micro lens is about 0.066 mm. In some embodiments, an effective numerical aperture of the micro lens is between about 0.2 and about 0.4. In some embodiments, the sample chamber has a depth of between about 5 µm and about 20 µm. In some embodiments, the sample chamber has a volume of between about 0.01 µl and about 100 µl. In some embodiments, the at least one surface of the sample chamber is optically transparent over the wavelength range of about 400 nm to about 2,500 nm. In some embodiments, the first component has a length between about 40 mm and about 80 mm. In some embodiments, the first component has a width of between about 10 mm and about 25 mm. In some embodiments, the first component has a thickness of between about 1.5 mm and about 2.5 mm. In some embodiments, the first component is fabricated from soda lime glass, borosilicate glass, fused silica, cyclic olefin copolymer (COC), cyclic olefin polymer (COP), poly(methyl methacrylate) (PMMA), Tyril™ 867E styrene and acrylonitrile (SAN) resin, or any combination thereof. In some embodiments, the second component is fabricated from soda lime glass, borosilicate glass, fused silica, cyclic olefin copolymer (COC), cyclic olefin polymer (COP), poly (methyl methacrylate) (PMMA), Tyril™ 867E styrene and acrylonitrile (SAN) resin, or any combination thereof. In some embodiments, the device is a single-use disposable.

Also disclosed herein are motility analysis systems comprising: a) a sample-containing device comprising: i) a substantially planar first component, wherein the first component comprises a first alignment feature and a sample chamber configured to hold a sperm sample to be imaged, and wherein at least one surface of the sample chamber is optically transparent; and ii) a removable, substantially planar second component that forms a lid for the sample chamber and that comprises a micro lens, wherein the micro lens is optically aligned with the sample chamber and contacts the sperm sample or is placed in close proximity to the sperm sample when the removable second component is positioned in the first alignment feature; and b) an imaging system, wherein the imaging system comprises: i) a light source configured to direct light through the optically transparent surface of the sample chamber; ii) an image sensor chip configured to acquire a series of one or more image(s) from light transmitted, scattered, or emitted by the sample and collected by the micro lens; iii) a processor configured to perform initial processing and storage of image data for the series of one or more image(s) acquired by the image sensor chip; and iv) a housing, wherein the housing comprises a second alignment feature and encloses the light source, and wherein the image sensor chip, micro lens, sample chamber, and light source are optically aligned when the device is positioned in the second alignment feature.

In some embodiments, the first component comprises two or more sample chambers. In some embodiments, the housing does not enclose the image sensor chip. In some embodiments, the micro lens is a ball lens, a cylindrical lens, or a rectangular lens. In some embodiments, the micro lens is a ball lens and has a diameter of between about 0.5 mm and about 2 mm. In some embodiments, the micro lens is fabricated from H-ZLaF71, LaSFN9, or S-LAH79. In some embodiments, an effective focal length of the micro lens is between about 0.25 mm and about 1 mm. In some embodiments, an effective focal length of the micro lens is about 0.82 mm. In some embodiments, a back focal length of the micro lens is between about 0.01 mm to about 0.1 mm. In some embodiments, a back focal length of the micro lens is about 0.066 mm. In some embodiments, an effective numerical aperture of the micro lens is between about 0.2 and about 0.4. In some embodiments, the sample chamber has a depth of between about 5 µm and about 20 µm. In some embodiments, the sample chamber has a total volume of between about 0.01 µl and about 100 µl. In some embodiments, the at least one surface of the sample chamber is optically transparent over the wavelength range of about 400 nm to about 2,500 nm. In some embodiments, the first component has a length between about 40 mm and about 80 mm. In some embodiments, the first component has a width of between about 10 mm and about 25 mm. In some embodiments, the first component has a thickness of between about 1.5 mm and about 2.5 mm. In some embodiments, the first component is fabricated from soda lime glass, borosilicate glass, fused silica, cyclic olefin copolymer (COC), cyclic olefin polymer (COP), acrylic, Tyril™ 867E styrene and acrylonitrile (SAN) resin, or any combination thereof. In some embodiments, the second component is fabricated from soda lime glass, borosilicate glass, fused silica, cyclic olefin copolymer (COC), cyclic olefin polymer (COP), acrylic, Tyril™ 867E styrene and acrylonitrile (SAN) resin, or any combination thereof. In some embodiments, the device is a single-use disposable. In some embodiments, the light source is an LED, high intensity LED, or laser diode. In some embodiments, the light source provides light in the wavelength range from about 400 nm to about 700 nm. In some embodiments, the light source is configured to stop functioning after a specified number of exposure cycles. In some embodiments, the specified number of exposure cycles is less than or equal to 1,000. In some embodiments, the specified number of exposure cycles is less than or equal to 100. In some embodiments, the image sensor chip is a charge-coupled device (CCD) image sensor or a complementary metal-oxide-semiconductor (CMOS) image sensor. In some embodiments, the image sensor chip comprises an array of 4,000×3,000 image pixels, 4032×3024 image pixels, or 5312×2988 image pixels. In some embodiments, a longest dimension of an individual image pixel in the array of image pixels is less than 1.55 µm. In some embodiments, a total magnification of the sperm sample image is between about 10× and about 100×. In some embodiments, a field-of-view of the imaging system is about 1 mm×1 mm. In some embodiments, a depth-of-field of the imaging system is between about 5 µm and about 20 µm. In some embodiments, the imaging system further comprises at least one additional lens, mirror, dichroic reflector, prism, optical filter, optical fiber, aperture, light source, image sensor chip, or any combination thereof. In some embodiments, the imaging assembly is configured to acquire bright-field, dark-field, phase contrast, or fluorescence images. In some embodiments, the series of one or more image(s) acquired by the image sensor chip comprises video data. In some embodiments, the light source is configured to function as a strobe light that is synchronized with image acquisition, and the image sensor chip is configured to acquire images using an exposure time of less than 40 msec. In some embodiments, the initial processing of image data comprises applying a contrast adjustment algorithm, a noise reduction algorithm, a flat-field or vignetting correction algorithm, an optical distortion correction algorithm, an optical aberration correction algorithm, a data compression algorithm, or any combination thereof to the series of one or more image(s). In some embodiments, the image sensor chip and processor of the imaging system are provided by a smart phone, and wherein the housing comprises a third alignment feature or adjustable fixture that facilitates optical alignment of the image sensor chip of the smart phone with the micro lens, sample chamber, and light source. In some embodiments, image acquisition by the image sensor chip is controlled by a software application running on the smart phone. In some embodiments, the software application performs further processing of the image data that comprises performing an edge detection algorithm, an image segmentation algorithm, a centroid calculation algorithm, a feature detection algorithm, a pattern detection algorithm, a motion tracking algorithm, a mathematical analysis algorithm, a statistical analysis algorithm, or any combination thereof. In some embodiments, the further processing of the image data provides a test result for total sperm count, total sperm concentration, motile sperm count, motile sperm concentration, average sperm motility or velocity, sperm motility or velocity for the motile fraction, sperm morphology, presence of sperm morphological defects, number of sperm morphological defects, or any combination thereof. In some embodiments, the software application is configured to upload image data or a test result to a cloud-based database. In some embodiments, all or a portion of the image processing is performed in the cloud using a cloud-based image processing algorithm. In some embodiments, one or more test results stored locally or stored in the cloud-based database are used to make an agricultural diagnostic decision, to make a clinical diagnostic decision, to guide a therapeutic decision, to monitor a therapeutic treatment regimen, or to make a marketing decision. In some embodiments, the housing comprises an upper component and a lower component that are separable, and wherein the lower component further comprises features configured for storage of one or more sample-containing devices. In some embodiments, a longest dimension of the housing is less than or equal to about 170 mm. In some embodiments, a total volume of the housing is less than or equal to about 1,300 cm³. In some embodiments, the imaging system is designed to become non-functional after a specified number of uses. In some embodiments, the specified number of uses is less than or equal to 1,000. In some embodiments, the specified number of uses is less than or equal to 100.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3B—side view) illustrating one non-limiting example of a device for use in imaging sperm cells. The dimensions are in units of millimeters.

FIG. 25 provides one non-limiting example of sperm motility analysis results displayed on a smartphone screen by the SpermCell application.

FIG. 27B—high magnification) collected for sperm samples placed in a Makler® counting chamber. Sperm cell counts were performed manually or by processing of the image data using SpermCell image processing and sperm motility analysis software.

FIG. 28 shows one non-limiting example of SpermCell sperm motility analysis software validation data.

DETAILED DESCRIPTION

Figure 1:
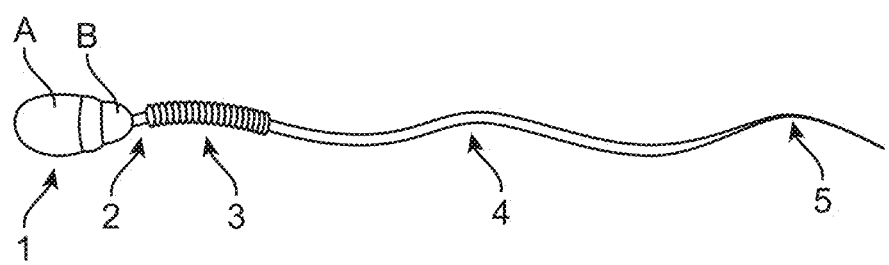
FIG. 1 provides a schematic illustration of a sperm cell (adapted from Di Caprio, et al. (2015), "Holographic Imaging of Unlabelled Sperm Cells for Semen Analysis: A Review", J. Biophotonics 8(10):779-789.

Disclosed herein are methods, devices, and systems for imaging sperm samples (or other motile cells and microorganisms) and performing a motility and/or morphology analysis.

In one aspect of the present disclosure, a sample-containing device designed for use in imaging samples is described. In some embodiments, the device comprises: (i) a substantially planar first component that further comprises an alignment feature and a sample chamber configured to hold the sample to be imaged; and (ii) a removable, substantially planar second component that forms a lid for the sample chamber and that comprises a micro lens, wherein the micro lens is optically aligned with the sample chamber and contacts the sample (or is placed in close proximity to the sample) when the removable second component is positioned in the alignment feature. In some preferred embodiments, the sample-containing device may comprise two or more sample chambers. In some preferred embodiments, the micro lens may be a ball lens that enables short focal length, high numerical aperture imaging of the sample. In some preferred embodiments, the sample-containing device may be a single use, disposable device.

In another aspect of the present disclosure, a compact imaging system designed to work with the disclosed sample-containing devices is described. In some embodiments, the imaging system comprises: (i) a light source configured to direct light through an optically transparent surface of the sample chamber within the sample-containing device; (ii) an image sensor chip configured to acquire a series of one or more image(s) from light transmitted, scattered, or emitted by the sample and collected by the micro lens; (iii) a processor configured to perform initial processing and storage of image data for the series of one or more image(s) acquired by the image sensor chip; and (iv) a housing, wherein the housing comprises a second alignment feature and encloses the light source, and wherein the image sensor chip, micro lens, sample chamber, and light source are optically aligned when the device is positioned in the second alignment feature. In some preferred embodiments, the housing encloses the light source and other components of the illumination system (i.e., a sub-assembly of the compact imaging system), but does not enclose the image sensor. In some preferred embodiments, the image sensor chip and processor of the imaging system are provided by a smart phone. In some preferred embodiments, the light source is configured to stop functioning after a specified number of exposure cycles. In some preferred embodiments, the illumination sub-assembly or the entire compact imaging system is designed to become non-functional after a specified number of uses (or exposure cycles). In some preferred embodiments, the housing comprises an upper component and a lower component that are separable, and wherein the lower component further comprises features configured for storage of one or more sample-containing devices.

In a third aspect of the present disclosure, a motility analysis system for imaging sperm samples (or other motile cells and microorganisms) and performing a motility and/or morphology analysis is described. In some embodiments, the motility analysis system may comprise (i) a sample-containing device as described above, (ii) a compact imaging system as described above, and (iii) image processing and analysis software. In some preferred embodiments, the initial processing of image data performed by the processor (which may be supplied by a smart phone) comprises applying a contrast adjustment algorithm, a noise reduction algorithm, a flat-field or vignetting correction algorithm, an optical distortion correction algorithm, an optical aberration correction algorithm, a data compression algorithm, or any combination thereof to the series of one or more image(s). In some preferred embodiments, the processor (which may be supplied by a smart phone) may perform further processing of the image data to provide a test result for total sperm count, total sperm concentration, motile sperm count, motile sperm concentration, average sperm motility or velocity, sperm motility or velocity for the motile fraction, presence of morphological defects, number of morphological defects, or any combination thereof. In some embodiments, all or a portion of the image processing may be performed by the local processor, or alternatively, all or a portion of the image processing may be performed remotely or in the cloud.

In some preferred embodiments, software running on the processor of the compact imaging system (which may be provided by a smart phone in some cases) is configured to upload image data or a test result to a cloud-based database. In some preferred embodiments, one or more test results stored locally or stored in a cloud-based database are used to make an agricultural diagnostic decision, to make a clinical diagnostic decision, to guide a therapeutic decision, to monitor a therapeutic treatment regimen, or to make a marketing decision.

Examples of applications for the disclosed methods, devices, and systems include, but are not limited to, basic biological research directed to the study of motile microorganisms, diagnosis of reproductive issues in farm animals and race horses, quality assessment of semen samples (fresh or frozen) at stud farms and farm animal breeding facilities that utilize artificial insemination techniques, and diagnosis of male reproductive problems in rural areas or smaller urban centers. In some instances, the disclosed methods, devices and, systems may be used as a basic tool for biological research or as an educational toy, e.g., for imaging and studying bacteria, algae, yeast, cells, unicellular ciliates such a paramecium, small insects, and the like in samples collected from culture plates, ponds, sea water, rain water, rain drops, bodily fluids such as blood or plasma, etc. In some instances, images and/or video data may be shared over the web using social networking tools such as YouTube, Instagram, or Facebook.

Definitions

The present disclosure provides methods, devices, and systems for imaging and performing a morphological and/or motility analysis of sperm (or other motile cells and microorganisms). Various aspects of the invention described herein may be applied to any of the particular applications set forth below or for any other types of basic research, environmental monitoring, agricultural or veterinary diagnostics, or clinical diagnostics applications. It shall be understood that different aspects of the invention can be appreciated individually, collectively, or in combination with each other.

Unless otherwise defined, all technical terms used herein have the same meaning as commonly understood by one of ordinary skill in the art in the field to which this disclosure belongs. As used in this specification and the appended claims, the singular forms "a", "an", and "the" include plural references unless the context clearly dictates otherwise. Any reference to "or" herein is intended to encompass "and/or" unless otherwise stated.

Samples:

As noted above, the disclosed methods, devices, and systems may be used for imaging any of a variety of motile cells and organisms, including but not limited to spermatozoa, bacteria, single cell microorganisms, etc. In some embodiments, the disclosed methods, devices, and systems may be used for imaging other types of biological samples, e.g., blood samples, sputum samples, tissue samples, and the like. In some embodiments, the disclosed methods, devices, and system may be used for imaging non-biological samples such as water samples collected for environmental monitoring.

Sperm Cell Morphology and Motility:

In a preferred embodiment, the disclosed methods, devices, and systems may be used for imaging sperm cells. The structure of a sperm cell is illustrated in FIG. 1. Mammalian sperm cells consist of a head region (1), neck region (2), a middle piece (3), tail (4), and end piece (5). The head region (1) contains the nucleus which comprises densely-coiled fibers of chromatin containing a haploid set of chromosomes, and is partially covered anteriorly by an acrosome (A) which contains an array of hydrolytic enzymes used for penetrating the female egg. The remaining portion of the head is the post-acrosomal region (B). The neck (2) contains the sperm centriole. The middle piece (3) comprises a central filamentous core and an abundance of mitochondria engaged in the production of ATP. The tail (4) comprises an axial filament (axoneme) surrounded by cytoplasm and plasma membrane, and executes the lashing movements that propel the sperm cell. The back and forth lashing movement of the tail results from a cyclic longitudinal sliding motion between the anterior and posterior tubules that make up the axoneme, with the underlying process driven by the ATP produced in the mitochondria. The end piece (5) comprises the axial filament with no surrounding cytoplasm or plasma membrane. The flat, disc-shaped head of a human sperm cell is approximately 5.1 μm by 3.1 μm, with the tail being approximately 50 μm long. Sperm cells of different species may differ in overall size and head shape, as well as in swimming velocity, and pattern of motion (Amann & Waberski (2014)). The typical velocity of a sperm cell in a fluid medium ranges from about 1 to 4 mm/min. A number of studies have indicated that sperm morphology is the best predictor of outcome for natural fertilization, intra-uterine insemination, and in vitro fertilization (Di Caprio, et al. (2015)).

Abnormal Sperm Morphology and Motility:

Sperm cells may exhibit a variety of abnormal morphological and/or motility traits that may be negative indicators for successful fertilization outcomes. Examples include, but are not limited to, abnormally small (microcephalic) or large (macrocephalic) heads, misshapen heads, two-headed sperm cells, sperm having broken acrosomes, two-tailed sperm cells, abaxial (asymmetrically-attached or off-axis) tails, coiled tails, bent tails, tails comprising proximal or distal droplets of cytoplasm, the presence of nuclear vacuoles in the head, abnormally low swimming velocity, abnormally low fraction of motile sperm cells in a population of sperm cells, abnormally low concentrations of sperm cells in a semen sample, etc.

Some morphological defects give rise to abnormally low sperm motility. For example, sperm cells having bent tails may be associated with low sperm motility. The presence of sperm cells having bent tails in semen samples analyzed both before and after freezing may indicate a morphological defect that underlies a reproductive problem in the donor (Di Caprio, et al. (2015)). Alternatively, when this anomaly appears with high frequency only in semen samples that have been previously frozen, it may indicate that the sperm have been subjected to hypo-osmotic stress through use of an inadequate freezing process.

The presence of sperm with broken acrosomes is another potential indicator of incorrect sperm handling during the freezing process (Di Caprio, et al. (2015)). Although uncommon in fresh semen, sperm with broken acrosomes can be present at high percentages in semen samples that were improperly frozen.

Sample Preparation:

Any of a variety of sample preparation techniques known to those of skill in the art may be used with the disclosed methods, devices, and systems, with the sample preparation technique typically determined by the type of sample to be imaged and analyzed. For CASA analysis, sperm may be examined after a standard dilution of neat semen in a complex extender (a liquid diluent which is added to semen to preserve its fertilizing ability) or in a simple salt solution (Amann & Waberski (2014)). The use of defined, standardized conditions for sperm motility and/or morphological analysis facilitates comparison of the results with those for other semen samples.

In some embodiments, cryogenically frozen semen samples may simply be allowed to thaw prior to performing imaging and analysis. Cryoprotected samples may have been previously frozen in any of a variety of media known to those of skill in the art including, but not limited to, an extender solution, an isotonic solution, egg yolk, or any combination thereof. Some semen samples, e.g., those frozen in egg yolk or various animal semen samples that contain high concentrations of sperm, may need to be diluted in, for example, an extender solution, phosphate buffered saline (PBS), an isotonic solution, or any combination thereof, prior to performing imaging and analysis.

In some embodiments, morphological or motility analysis of sperm may be performed in a wet preparation after exposing the sperm to, for example, a contrast agent, a dye molecule, or a fluorophore. In some embodiments, morphological analysis of sperm may be performed using a dry preparation stained with, for example, a contrast agent, a dye molecule, or a fluorophore.

Figure 2:
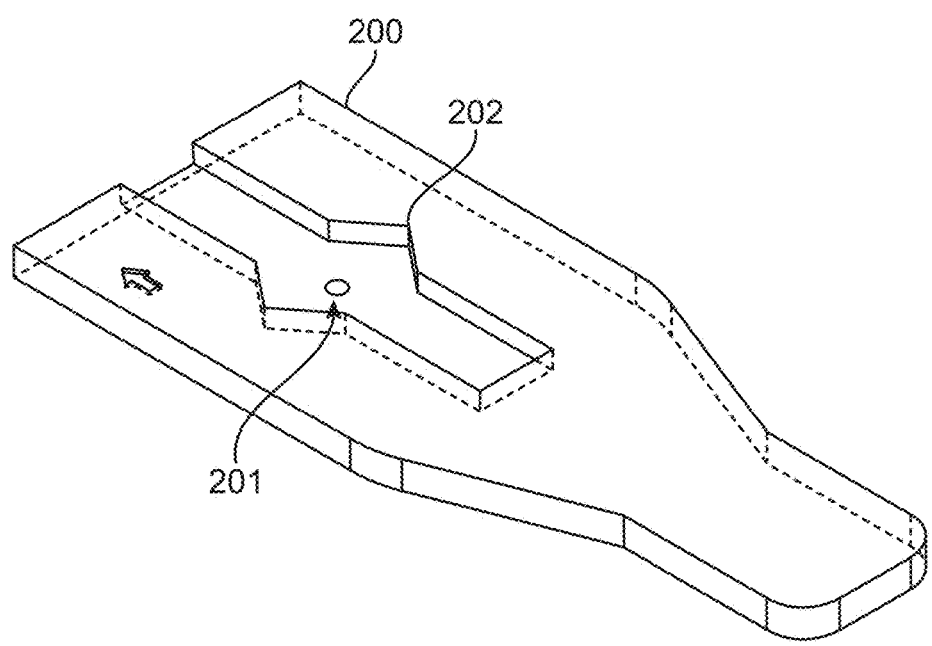
FIG. 2 provides an isometric drawing illustrating one non-limiting example of a device for use in imaging sperm cells or other motile organisms, e.g., bacteria or protozoa. A small microchamber (201) is used to hold a droplet of the sample to be imaged.

Sample Imaging Device:

FIGS. 2-5 illustrate one non-limiting example of a design for the imaging devices of the present disclosure. As indicated in FIG. 2, the device for imaging sperm cells (or other samples) comprises a first component (200) (or "chip") that is substantially planar and that further comprises at least one sample chamber (201) and at least one alignment feature (202), wherein at least one surface of the sample chamber is optically transparent. In some embodiments, the device may comprise a plurality of sample chambers (or sample compartments). For example, in some embodiments, the device may comprise at least 1 sample chamber, at least 2 sample chambers, at least 3 sample chambers, at least 4 sample chambers, at least 5 sample chambers, at least 6 sample chambers, at least 7 sample chambers, at least 8 sample chambers, at least 9 sample chambers, or at least 10 sample chambers. The device also comprises a removable second component (not shown in FIG. 2) that forms a lid for the at least one sample chamber, as will be described in more detail below. In some embodiments, the disclosed sample imaging devices may be single-use, disposable devices.

As viewed from the top, the at least one sample chamber (201) may have any of a variety of suitable geometries including, but are not limited to, square, rectangular, triangular, circular, elliptical, etc., or any combination thereof. In some embodiments, the sample chamber may comprise geometric elements drawn from two or more basic geometrical shapes, e.g., a rectangular shape overlaid with a square shape that has been rotated around an axis that is perpendicular to the plane of the rectangle and square, as illustrated in FIG. 2.

In general, the depth of the at least one sample chamber may range from about 1 µm to about 1 mm. In some embodiments, the depth of the at least one sample chamber may be at least 1 µm, at least 5 µm, at least 10 µm, at least 20 µm, at least 30 µm, at least 40 µm, at least 50 µm, at least 100 µm, at least 200 µm, at least 300 µm, at least 400 µm, at least 500 µm, at least 750 µm, or at least 1 mm. In some embodiments, the depth of the at least one sample chamber may be at most 1 mm, at most 750 µm, at most 500 µm, at most 400 µm, at most 300 µm, at most 200 µm, at most 100 µm, at most 50 µm, at most 40 µm, at most 30 µm, at most 20 µm, at most 10 µm, at most 5 µm, or at most 1 µm. Any of the lower and upper values described in this paragraph may be combined to form a range included within the present disclosure, for example, the depth of the at least one sample chamber may range from about 20 µm to about 40 µm. Those of skill in the art will recognize that the depth of the at least one sample chamber may have any value within this range, e.g., about 12 µm.

For sperm motility analysis using commercially-available CASA systems, disposable chambers that are loaded using capillary action and that have a carefully controlled depth of 20 µm or 10 µm are typically used (Amann & Waberski (2014). The shallow depth of the sample chamber confines the motion of the sperm cells to the useful depth-of-field of the imaging system. In some cases, this means that sperm from some species may not swim in their normal manner, e.g., bull sperm may require unrestricted freedom of motion of at least 12 µm in each direction from the plane of the head (i.e., a minimum chamber depth of about 24 µm) in order to accommodate the motion of the tail and swim normally. Furthermore, close proximity of the sperm cells to a sample chamber surface may alter sperm motility parameters and patterns of motion due to interactions with the surface. Thus, in some embodiments, sample imaging devices comprising different sample chamber depths may be provided for analysis of sperm from different species. In some embodiments, the imaging device may provide a plurality of sample chambers, wherein different sample chambers of the plurality have different depths.

In general, the volume of the at least one sample chamber may range from about 0.01 µl to about 100 µl. In some embodiments, the volume of the at least one sample chamber may be at least 0.01 µl, at least 0.05 µl, at least 0.1 µl, at least 0.5 µl, at least 1 µl, at least 5 µl, at least 10 µl, at least 20 µl, at least 30 µl, at least 40 µl, at least 50 µl, at least 60 µl, at least 70 µl, at least 80 µl, at least 90 µl, or at least 100 µl. In some embodiments, the volume of the at least one sample chamber may be at most 100 µl, at most 90 µl, at most 80 µl, at most 70 µl, at most 60 µl, at most 50 µl, at most 40 µl, at most 30 µl, at most 20 µl, at most 10 µl, at most 5 µl, at most 1 µl, at most 0.5 µl, at most 0.1 µl, at most 0.05 µl, or at most 0.01 µl. Any of the lower and upper values described in this paragraph may be combined to form a range included within the present disclosure, for example, the volume of the at least one sample chamber may range from about 20 µl to about 90 µl. Those of skill in the art will recognize that the volume of the at least one sample chamber may have any value within this range, e.g., about 75 µl. In some embodiments, two or more sample chambers of a plurality of sample chambers may have the same sample chamber volume. In some embodiments, two or more sample chambers of a plurality of sample chambers may have different sample chamber volumes.

The at least one alignment feature (202) is designed to mate with and facilitate correct positioning of the removable second component (i.e., the lens holder) that forms a lid for the at least one sample chamber. In some embodiments, the first component comprises at least 1 alignment feature, at least 2 alignment features, at least 3 alignment features, at least 4 alignment features, at least 5 alignment features, at least 6 alignment features, at least 7 alignment features, at least 8 alignment features, at least 9 alignment features, or at least 10 alignment features. The alignment feature may have any suitable geometry and any suitable dimensions that serve to ensure proper relative positioning of the second component and the first component. For example, the alignment feature (202) may have a square or diamond shape (i.e., comprising the opposite corners of a square or diamond shape), as illustrated in FIG. 2, or it may comprise one or more rectangular features, triangular features, slot-like features, semi-circular features, partially circular or arc-shaped features, etc.

Figure 3A:
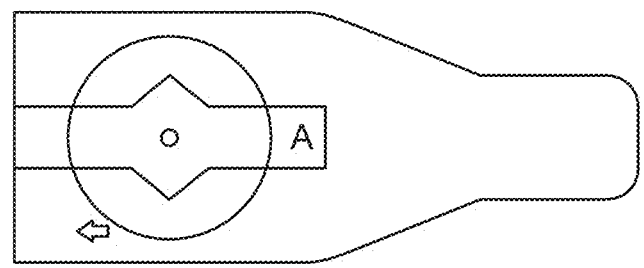
FIGS. 3A-B provide mechanical drawings (FIG. 3A—top view.

FIG. 3A provides a mechanical drawing (top view) of the device illustrated in FIG. 2. In some embodiments, the footprint of the device as viewed from the top may be substantially rectangular. In some embodiments, the footprint of the device as viewed from the top may comprise any of a variety of suitable geometries including, but are not limited to, square, rectangular, triangular, circular, elliptical, etc., or any combination thereof. In some embodiments, the device as viewed from the top may comprise geometric elements drawn from two or more basic geometrical shapes, e.g., a modified rectangle comprising a narrowed end portion or tab, as indicated in FIG. 3A.

In some embodiments, the longest dimension of the device (e.g., the length) when viewed from the top may range from about 10 mm to about 100 mm. In some embodiments, the longest dimension of the device (i.e., of the first component that comprises a sample chamber) may be at least 10 mm, at least 20 mm, at least 30 mm, at least 40 mm, at least 50 mm, at least 60 mm, at least 70 mm, at least 80 mm, at least 90 mm, or at least 100 mm. In some embodiments, the longest dimension of the device may be at most 100 mm, at most 90 mm, at most 80 mm, at most 70 mm, at most 60 mm, at most 50 mm, at most 40 mm, at most 30 mm, at most 20 mm, or at most 10 mm. Any of the lower and upper values described in this paragraph may be combined to form a range included within the present disclosure, for example, the longest dimension of the device may range from about 40 mm to about 70 mm. Those of skill in the art will recognize that the longest dimension of the device may have any value within this range, e.g., about 62 mm. In general, the longest dimension of the device may be any length so long as the device can still be conveniently handled and positioned in the compact imaging system. For example, in some embodiments, the device may have a long dimension as small as about 1 mm, about 2 mm, about 3 mm, about 4 mm, about 5 mm, about 6 mm, about 7 mm, about 8 mm, or about 9 mm.

In some embodiments, the narrowest dimension of the device (e.g., the width) when viewed from the top may range from about 5 mm to about 40 mm. In some embodiments, the narrowest dimension of the device may be at least 5 mm, at least 10 mm, at least 15 mm, at least 20 mm, at least 25 mm, at least 30 mm, at least 35 mm, or at least 40 mm. In some embodiments, the narrowest dimension of the device may be at most 40 mm, at most 35 mm, at most 30 mm, at most 25 mm, at most 20 mm, at most 15 mm, at most 10 mm, or at most 5 mm. Any of the lower and upper values described in this paragraph may be combined to form a range included within the present disclosure, for example, the narrowest dimension of the device may range from about 10 mm to about 30 mm. Those of skill in the art will recognize that the narrowest dimension of the device may have any value within this range, e.g., about 12 mm. As in the case of the long dimension, in general the narrowest dimension of the device may be any length so long as the device can still be conveniently handled and positioned in the compact imaging system. For example, in some embodiments, the device may have a narrowest dimension as small as about 1 mm, about 2 mm, about 3 mm, or about 4 mm.

Figure 3B:
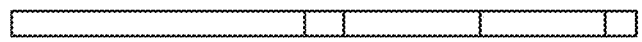

FIG. 3B provides a mechanical drawing (side view) of the device illustrated in FIG. 3A. In some embodiments, the overall thickness of the device (including the removable second component when positioned in the alignment feature of the first component) may range from about 1 mm to about 3 mm. In some embodiments, the overall thickness of the device may be at least 1 mm, at least 1.25 mm, at least 1.5 mm, at least 1.75 mm, at least 2 mm, at least 2.25 mm, at least 2.5 mm, at least 2.75 mm, or at least 3 mm. In some embodiments, the overall thickness of the device may be at most 3 mm, at most 2.75 mm, at most 2.5 mm, at most 2.25 mm, at most 2 mm, at most 1.75 mm, at most 1.5 mm, at most 1.25 mm, or at most 1 mm. Any of the lower and upper values described in this paragraph may be combined to form a range included within the present disclosure, for example, the overall thickness of the device may range from about 1.25 mm to about 2.5 mm. Those of skill in the art will recognize that the overall thickness of the device may have any value within this range, e.g., about 2.55 mm.

Figure 4:
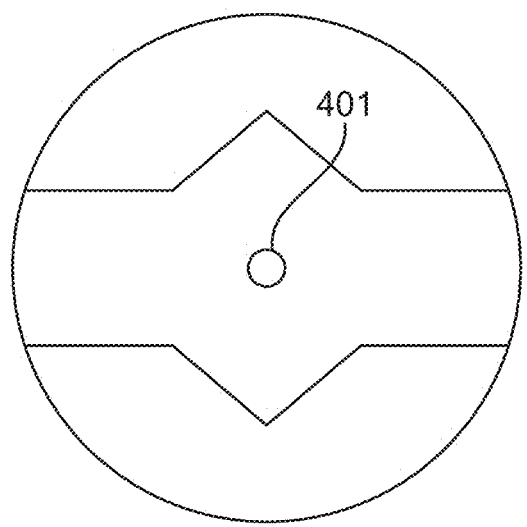
FIG. 4 provides a detail view of the sample chamber (401) of the device shown in FIGS. 3A-B. Dimensions are in millimeters.

FIG. 4 provides a detail view of the alignment feature on the top side of the device shown in FIG. 3A. The detail view illustrates the alignment of a micro lens (mounted in the removable second component (or "lens holder") that forms the lid of the sample chamber) with the sample chamber 401. In this non-limiting example, the sample chamber 401 has a 1.5 mm diameter and a depth when the lid is in position of 0.01 mm (or 10 µm). In some embodiments, an annular region of the surface comprising the bottom of the sample chamber may be rendered opaque by means of a printed or deposited layer of an opaque material (e.g., an ink layer, pigmented polymer coating, a metal layer, etc.), thereby restricting the light passing through the sample and into the micro lens to that area that provides the clearest image.

Figure 5:
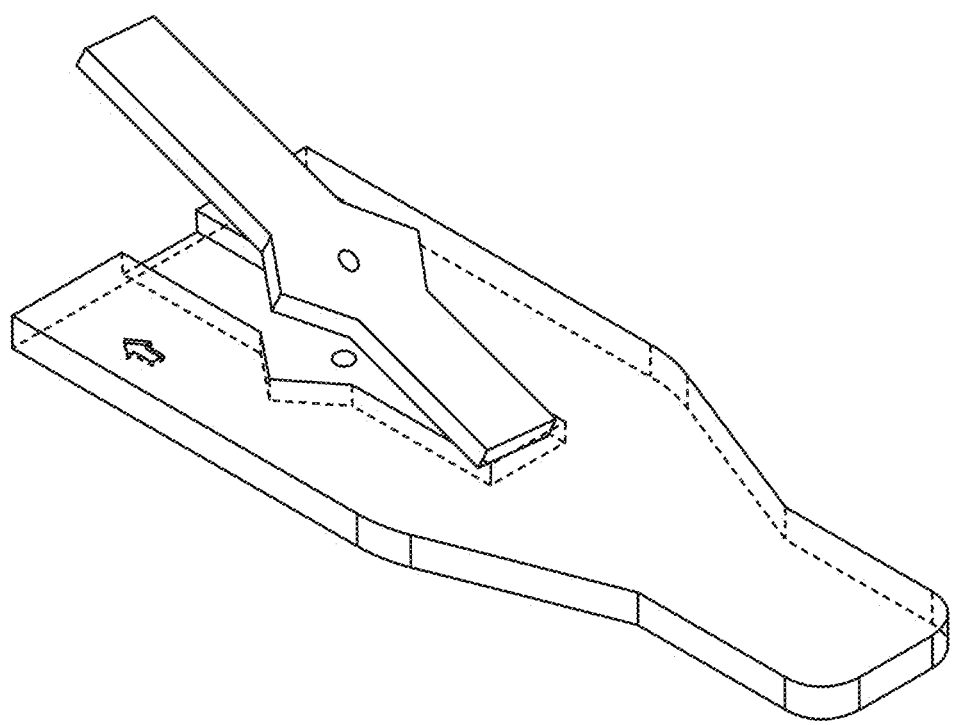
FIG. 5 illustrates the placement of a lens holder on the sample imaging device of FIGS. 3A-B to form a lid for the sample chamber and bring a micro lens into contact with the sample or into close proximity to the sample.

FIG. 5 illustrates the placement of a lens holder on the sample imaging device of FIGS. 3A-B to form a lid for the sample chamber and bring a micro lens into contact with or close proximity to the sample. As indicated in the figure, in some embodiments, a logo, serial number, or other marking may be embossed, molded, or machined on a top, side, and/or bottom surface of the device and/or lens holder.

Figure 6:
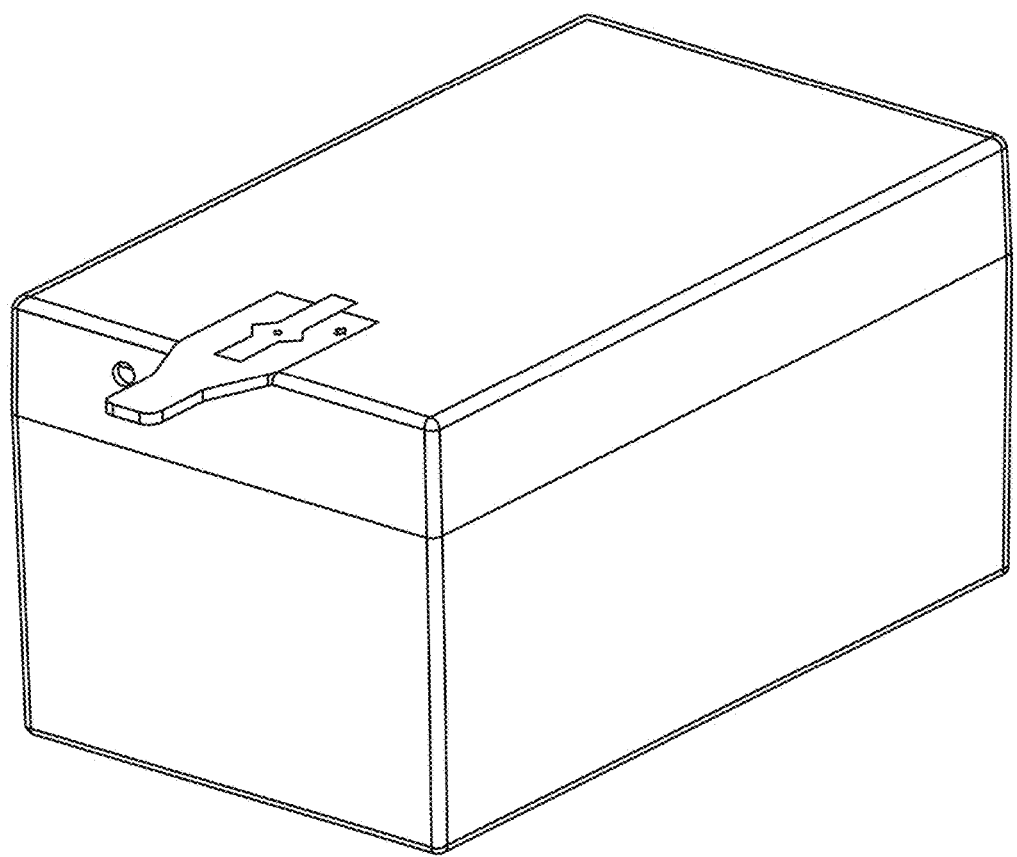
FIG. 6 illustrates the placement of the sample imaging device with lens holder in an alignment feature on the housing of an illumination sub-assembly that forms part of a compact imaging system used to image the sample.

FIG. 6 illustrates the placement of the sample imaging device with lens holder in an alignment feature on the housing of an illumination sub-assembly that forms part of a compact imaging system used to image the sample.

Figure 7:
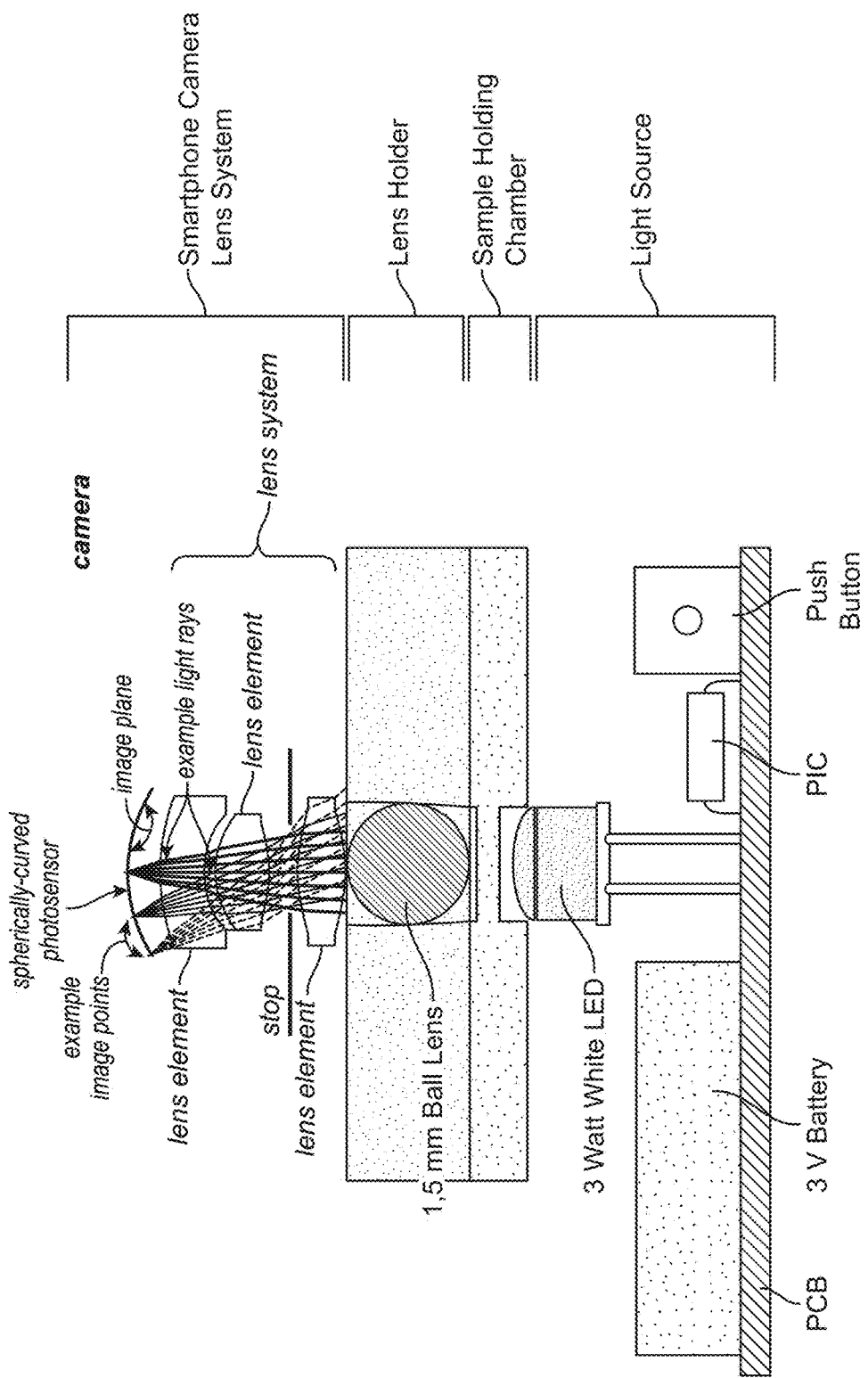
FIG. 7 provides a non-limiting example of an imaging system that includes an illumination sub-assembly comprising an LED light source, a sample imaging device comprising a sample chamber and lens holder that brings a micro lens into contact with the sample (or into close proximity to the sample), and imaging optics comprising an image sensor. In this non-limiting example, the imaging optics and image sensor are provided by a smartphone camera system.

FIG. 7 provides a non-limiting example of an imaging system that includes an illumination sub-assembly comprising an LED light source, a sample imaging device comprising a sample chamber and lens holder that brings a micro lens into contact with or close proximity to the sample, and imaging optics comprising an image sensor. In this non-limiting example, the imaging optics and image sensor are provided by a smartphone camera system. White light emitted by an LED light source is directed through a window or aperture in the sample imaging device, through the sample chamber wherein the sample is in contact with or in close proximity to a ball lens that collects scattered or transmitted light passing through the sample, and is imaged by the camera system of the smartphone. In some embodiments, the imaging system may further comprise additional lenses, mirrors, optical filters, dichroic reflectors, prisms, apertures, LED or other light sources, image sensors, etc., that are not shown in FIG. 7.

Figure 8:
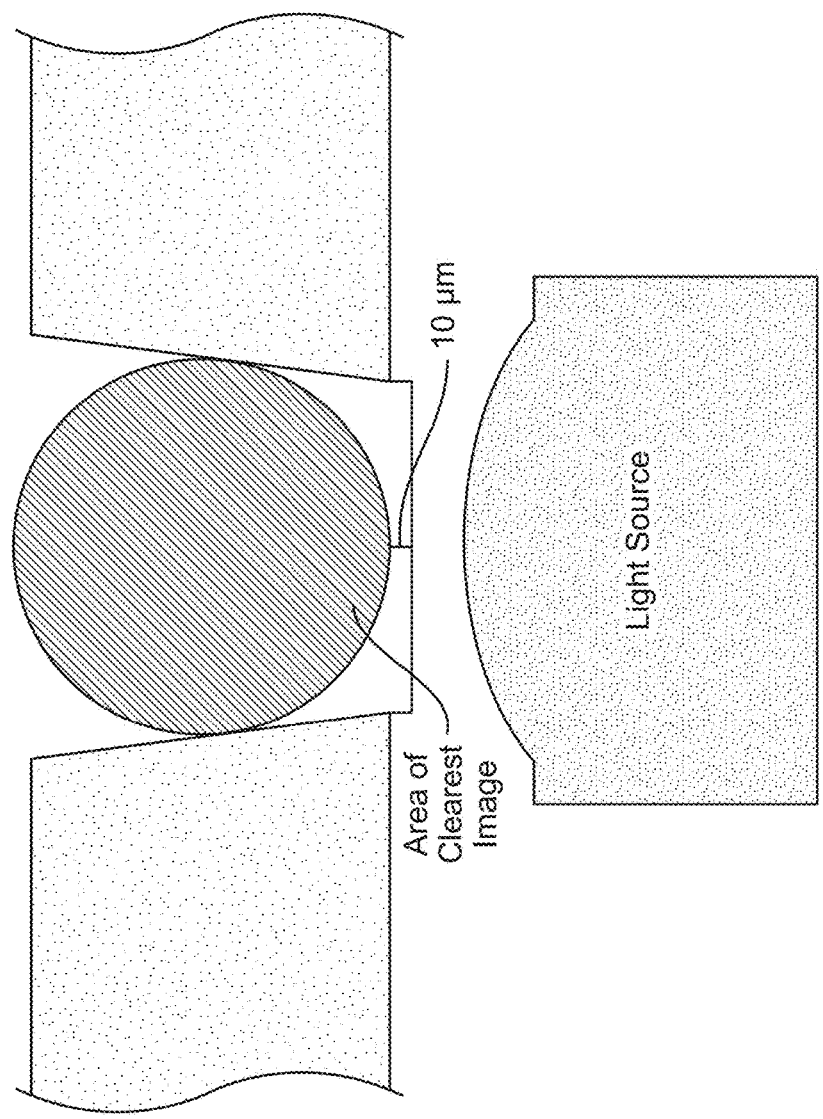
FIG. 8 provides a schematic cross-sectional view of a lens holder comprising a ball lens that is brought into contact with the sample (or into close proximity to the sample) in a sample chamber of 10 μm depth, and its positioning relative to an LED light source.

FIG. 8 provides a schematic cross-sectional view of a lens holder comprising a ball lens that is brought into contact with or close proximity to the sample in a sample chamber of 10 µm depth, and its positioning relative to an LED light source. Light transmitted through the sample chamber is collected by the ball lens and directed to imaging optics (not shown in this figure) that, in some embodiments, may be provided by the camera system of a smartphone. Light collected by and transmitted through a central zone of the ball lens (i.e., closest to the optical axis of the illumination/imaging system) may define an area of clearest image within the field-of-view of the imaging system.

Figure 9:
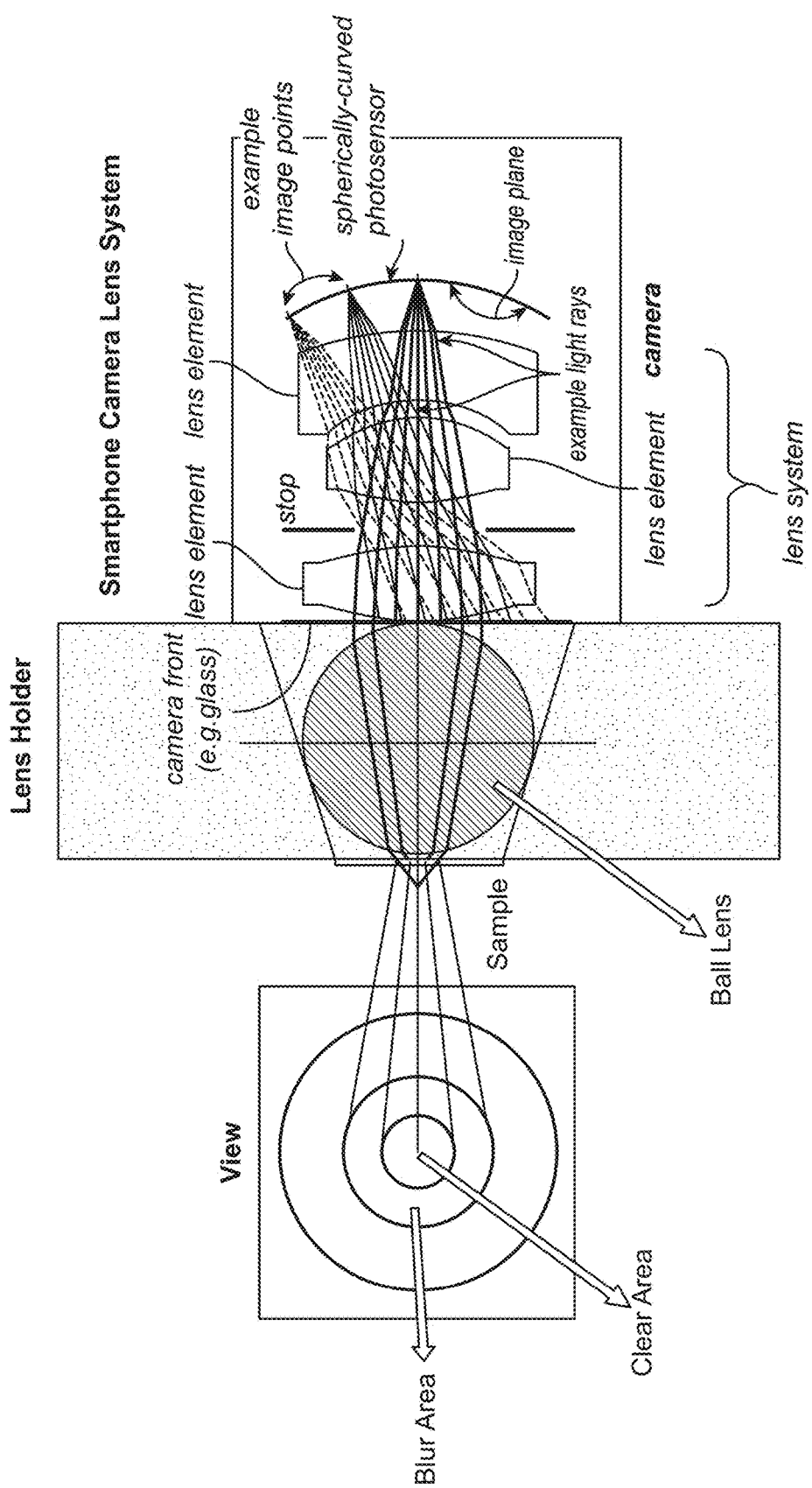
FIG. 9 provides a schematic drawing illustrating one non-limiting example of an optical design wherein a smart phone camera is used with the disclosed devices and systems for imaging of a sample. The use of a ball lens placed in contact with the sample (or into close proximity to the sample) to be imaged yields a central region of clear images surrounded by a blurred image zone.

FIG. 9 shows a cross-sectional view of the removable second component of the device that forms a lid for the sample chamber (201) when positioned within the alignment feature (202) of the first component (FIG. 2). As illustrated in FIG. 9, the sample chamber lid may also function as a lens holder, wherein a micro lens (e.g., a ball lens) is positioned within an aperture in the removable second component and press-fit or bonded in place, e.g., using an optical adhesive. The micro lens functions as an objective lens for imaging the sample, and is optically aligned with the sample chamber when the removable second component is positioned in the alignment feature. In some embodiments, the micro lens does not make contact with the sample when the removable second component (or lens holder) is positioned within the sample chamber opening and alignment feature of the first component. Rather, the micro lens may be brought into close proximity to the sample (e.g., within 0.1 µm, within 0.5 µm, with 1 µm, or within 2 µm of the sample) without directly contacting the sample. In preferred embodiments, the micro lens is placed in direct contact with the sample when the removable second component (or lens holder) is positioned within the sample chamber opening and alignment feature of the first component.

As noted above, light collected by and transmitted through a central zone of the ball lens (i.e., closest to the optical axis of the illumination/imaging system) may define an area of clearest image within the field-of-view of the imaging system. The area of clear image may further be surrounded by an area of blurred image. In some embodiments, one or more apertures may be positioned within the sample imaging device and/or with in the imaging system to restrict the light reaching the image sensor to that origination from the area of clearest image.

In some embodiments, the "micro lens" illustrated in FIG. 9 (designated as a "ball lens" in the figure) may comprise a compact optical assembly consisting of a single optical lens, two optical lenses, or three or more optical lenses. In some embodiments, the optical assembly may comprise one or more additional optical components, e.g., optical filters, apertures, etc. In a preferred embodiment, the micro lens comprises a ball lens or half-ball lens.

In some embodiments, the first component may comprise a micro lens and/or one or more additional optical components, e.g., optical filters, apertures, etc. Alternatively, in some embodiments, the second component may comprise a micro lens and/or one or more additional optical components, e.g., optical filters, apertures, etc. In some embodiments, both the first component and the second component may comprise a micro lens and/or one or more additional optical components, e.g., optical filters, apertures, etc.

In some embodiments, e.g., wherein the sample-containing device comprises two or more sample chambers, the first component and/or the second component of the sample-containing device may comprise two or more micro lenses, so that an imaging system may be used to simultaneously or serially capture images for two or more locations (i.e., at the positions of the two or more sample chambers) on the sample-containing device.

In some embodiments, the first and/or second components of the sample-containing device may further comprise one or more integrated CCD or CMOS image sensor chips. In some embodiments, such sample-containing devices that comprise one or more integrated CCD or CMOS image sensor chips may be disposable devices. In these embodiments, the size of the CCD or CMOS image sensor chip may preferably be comparable to or smaller than the size of the micro lens.

The micro lens, or one or more components of the micro lens assembly, may be fabricated from any of a variety of materials known to those of skill in the art. Examples include, but are not limited to, borosilicate glass, fused silica, polycarbonate (PC), cyclic olefin copolymer (COC), cyclic olefin polymer (COP), acrylic (e.g., poly(methyl methacrylate) (PMMA)), or any combination thereof. In a preferred embodiment, the micro lens, or one or more components of the micro lens assembly, may be fabricated from H-ZLaF71 (CDGM Glass Company, Ltd.; distributed by Universal Photonics, Central Islip, N.Y.). In other preferred embodiments, the micro lens, or one or more components of the micro lens assembly, may be fabricated from LaSFN9 (Newport Corp., Irvine, Calif.), S-LAH79 (Ohara Corp., Branchburg, N.J.), diamond, sapphire, or other high indices of refraction.

In general, the diameter of the micro lens may range from about 0.1 mm to about 3 mm. In some embodiments, the diameter of the micro lens may be at least 0.1 mm, at least 0.5 mm, at least 1.0 mm, at least 1.5 mm, at least 2.0 mm, at least 2.5 mm, or at least 3.0 mm. In some embodiments, the diameter of the micro lens may be at most 3.0 mm, at most 2.5 mm, at most 2.0 mm, at most 1.5 mm, at most 1.0 mm, at most 0.5 mm, or at most 0.1 mm. Any of the lower and upper values described in this paragraph may be combined to form a range included within the present disclosure, for example, the diameter of the micro lens may range from about 0.5 mm to about 2.5 mm. Those of skill in the art will recognize that the diameter of the micro lens may have any value within this range, e.g., about 1.5 mm.

In general, the effective focal length (EFL) (i.e., the distance from the mid-plane of the lens to the focal point) of the micro lens (or micro lens assembly) may range from about 0.3 mm to about 2.5 mm. In some embodiments, the effective focal length of the micro lens (or micro lens assembly) may be at least 0.3 mm, at least 0.5 mm, at least 1.0 mm, at least 1.5 mm, at least 2.0 mm, or at least 2.5 mm. In some embodiments, the effective focal length of the micro lens (or micro lens assembly) may be at most 2.5 mm, at most 2.0 mm, at most 1.5 mm, at most 1.0 mm, at most 0.5 mm, or at most 0.3 mm. Any of the lower and upper values described in this paragraph may be combined to form a range included within the present disclosure, for example, the effective focal length of the micro lens (or micro lens assembly) may range from about 0.5 mm to about 1.5 mm. Those of skill in the art will recognize that the effective focal length of the micro lens (or micro lens assembly) may have any value within this range, e.g., about 0.82 mm.

For a micro ball lens, the effective focal length may be calculated using equation 1:

$$EFL = \frac{nD}{4(n-1)} \quad (1)$$

where D is the diameter of the micro ball lens and n is the refractive index. For example, for a 1.0 mm diameter micro ball lens fabricated from sapphire (n=1.77), the effective focal length is 0.57 mm.

In general, the back focal length (BFL) (i.e., the distance between the back of the lens and the focal point) of the micro lens (or micro lens assembly) may range from about 0.001 mm to about 0.5 mm. In some embodiments, the back focal length of the micro lens (or micro lens assembly) may be at least 0.001 mm, at least 0.005 mm, at least 0.010 mm, at least 0.025 mm, at least 0.05 mm, at least 0.1 mm, at least 0.2 mm, at least 0.3 mm, at least 0.4 mm, or at least 0.5 mm. In some embodiments, the back focal length of the micro lens (or micro lens assembly) may be at most 0.5 mm, at most 0.4 mm, at most 0.3 mm, at most 0.2 mm, at most 0.1 mm, at most 0.05 mm, at most 0.025 mm, at most 0.010 mm, at most 0.005 mm, or at most 0.001 mm. Any of the lower and upper values described in this paragraph may be combined to form a range included within the present disclosure, for example, the back focal length of the micro lens (or micro lens assembly) may range from about 0.005 mm to about 0.1 mm. Those of skill in the art will recognize that the back focal length of the micro lens (or micro lens assembly) may have any value within this range, e.g., about 0.066 mm.

For a micro ball lens, the back focal length may be calculated using equation 2:

$$BFL = EFL - \frac{D}{2} \quad (2)$$

where, again, D is the diameter of the lens. For example, for a 1.0 mm diameter micro ball lens fabricated from sapphire (n=1.77), the back focal length is 0.075 mm. In general, the diameter and refractive index of the micro lens may be chosen so that the back focal length is less than or equal to the depth of the sample chamber. In some embodiments, the diameter and refractive index of the micro lens may be chosen so that the back focal length is less than or equal to about half of the sample chamber depth. In some embodiments, the diameter and refractive index of the micro lens may be chosen so that the back focal length is less than or equal to about a quarter of the sample chamber depth.

In some embodiments, an aperture positioned adjacent to the micro lens defines the effective numerical aperture of the micro lens. In some embodiments, the aperture may be provided by the second component of the device, e.g., if the second component is fabricated from an optically opaque material. In some embodiments, the effective numerical aperture of the micro lens may be determined by the extent to which the image is digitally zoomed, e.g., if the full optical field-of-view is not used for image capture or subsequent image processing. In general, the effective numerical aperture of the micro lens (or micro lens assembly) may range from about 0.2 to about 1.4. In some embodiments, the effective numerical aperture of the micro lens (or micro lens assembly) may be at least 0.2, at least 0.4, at least 0.6, at least 0.8, at least 1.0, at least 1.2, or at least 1.4. In some embodiments, the effective numerical aperture of the micro lens (or micro lens assembly) may be at most 1.4, at most 1.2, at most 1.0, at most 0.8, at most 0.6, at most 0.4, or at most 0.2. Any of the lower and upper values described in this paragraph may be combined to form a range included within the present disclosure, for example, the effective numerical aperture of the micro lens (or micro lens assembly) may range from about 0.6 to about 1.2. Those of skill in the art will recognize that the effective numerical aperture of the micro lens (or micro lens assembly) may have any value within this range, e.g., about 0.35.

In some embodiments, both the first component and the removable second component of the device may be fabricated as single layer, monolithic components in which sample chambers, alignment features, or other features may be embossed, molded, or machined. In some embodiments, the first component and/or second component may be fabricated as two or more layers of material that have been stacked, aligned, and bonded. Any of a variety of materials and fabrication techniques known to those of skill in the art may be used to fabricate the disclosed sample imaging devices, where the choice of material typically depends on the choice of fabrication technique or vice versa. Examples of suitable materials include, but are not limited to, soda lime glass, borosilicate glass, fused silica, cyclic olefin copolymer (COC), cyclic olefin polymer (COP), acrylic (e.g., poly(methyl methacrylate) (PMMA)), Tyril™ 867E styrene and acrylonitrile (SAN) resin, or any combination thereof. Examples of fabrication methods that may be used include, but are not limited to, micro-molding and micro-embossing, injection molding, CNC machining, bulk micro-machining techniques such as photolithography and wet chemical etching, plasma etching, deep reactive ion etching; laser micromachining; 3D printing or other direct write fabrication processes using curable materials; or any combination thereof.

Compact Imaging System:

FIG. 7 and FIG. 9 also provide one non-limiting example of an optical design wherein a smart phone camera is used with the disclosed sample-containing devices for imaging a sample. In general, the compact imaging system may comprise: (i) an illumination sub-assembly, (ii) the sample imaging system, and (iii) an optical imaging sub-assembly. In some embodiment the optical imaging sub-assembly may be provided by the camera system of a smartphone. As illustrated in FIG. 7, a light source mounted at a position below the sample containing device may be configured to direct imaging light through the sample chamber (i.e., using a trans-illumination design). Light that has been transmitted, reflected, scattered, or emitted by the sample, or sample components therein, is collected by the micro lens (e.g. a ball lens in preferred embodiments) and directed through the lens system of the smart phone camera to the latter's image sensor in order to capture images of the sample contained within the sample chamber. In some embodiments, the optical sub-assembly may comprise one or more additional lenses or other optical components and an image sensor instead of a smart phone camera. In some embodiments, the light source may be positioned above the sample containing device, and the sample-containing device component comprising the micro lens may be positioned on the lower side of the sample-containing device, with the image sensor or smart phone camera positioned on the side opposite the light source. In some embodiments, the light source and image sensor may be positioned on the same side of the sample-containing device, i.e., the side comprising the component in which the micro lens is incorporated, using an epi-illumination optical design. In some embodiments, the imaging system further comprises a housing which encloses the light source, and optionally also encloses the image sensor and/or one or more additional optical components. In some embodiments, the housing of the imaging system comprises a second alignment feature (i.e., an alignment feature in addition to the one used to align the first and second components of the sample-containing device) wherein the image sensor chip, micro lens, sample chamber, and light source are optically aligned when the sample-containing device is positioned in the second alignment feature. In some embodiments (e.g., those using a smart phone camera as the image sensor) the housing may comprise a third alignment feature that facilitates optical alignment of the image sensor chip of the smart phone camera with the micro lens, sample chamber, and light source. In some embodiments, the placement of a smart phone in the alignment feature of the housing also functions to bring the micro lens into contact with or close proximity to the sample in a sample chamber of the sample-containing device positioned in the optical imaging system. In some embodiments, the light source, illumination sub-assembly, or imaging system is designed to become non-functional after a specified number of uses or exposure cycles, e.g., by disablement of the light source (as will be described below), or by disablement of the image sensor (if included directly in the imaging system rather than provided by a smartphone), or by disablement of any other component required for the assembly to be used for imaging a sample. For example, in some embodiments, the light source, the illumination sub-assembly, or the compact imaging system may be designed to become non-functional after at most 10 uses, at most 20 uses, at most 30 uses, at most 40 uses, at most 50 uses, at most 60 uses, at most 70 uses, at most 80 uses, at most 90 uses, at most 100 uses, at most 200 uses, at most 300 uses, at most 400 uses, at most 500 uses, at most 600 uses, at most 700 uses, at most 800 uses, at most 900 uses, or at most 1,000 uses. In some embodiments, e.g., wherein the sample-containing device comprises two or more sample chambers, the compact imaging system may be configured to simultaneously or serially capture images for two or more locations on the sample-containing device.

Additional Optical Components:

As noted above, in addition to the light source, micro lens, and image sensor or smart phone camera, the illumination sub-assembly and/or the imaging sub-assembly may comprise one or more additional optical components. Examples of additional optical components include, but are not limited to, lenses, mirrors, dichroic reflectors, prisms, optical filters (e.g., colored glass filters, bandpass filters, interference filters, or notch filters), optical fibers, or apertures, as well as additional light sources, image sensor chips, or any combination thereof. In some embodiments, the imaging system may comprise one additional lens, two additional lenses, three additional lenses, four additional lenses, or five additional lenses. One or more of the optical components of the imaging system may be designed to correct for optical aberration, e.g., spherical aberration, chromatic aberration, etc.

Light Sources:

Any of a variety of light sources known to those of skill in the art may be used in constructing the illumination sub-assembly of the imaging system. Examples include, but are not limited to, light-emitting diodes (LEDs), high intensity LEDs, laser diodes, or any combination thereof. In some embodiments, the light source may be provided by the LED in a smartphone. In some embodiments, the imaging system may comprise one additional light source, two additional light sources, three additional light sources, four additional light sources, or five additional light sources. In some embodiments, the illumination light provided by one or more light sources may be delivered to the sample chamber at any angle relative to the optical axis of the imaging sub-assembly via a fiber optic or waveguide device integrated into the sample containing device or into the compact imaging system.

In some embodiments (e.g., where the imaging system or the illumination sub-assembly of the imaging system is a disposable or semi-disposable package), the one or more light sources may be configured to perform for a limited number of uses (i.e., wherein a single "use" corresponds to the capture of a series of one or more images used in performing a motility and/or morphological analysis of a single test sample, e.g., an exposure cycle). For example, in some embodiments, the one or more light sources may be configured to stop functioning after at most 10 uses, at most 20 uses, at most 30 uses, at most 40 uses, at most 50 uses, at most 60 uses, at most 70 uses, at most 80 uses, at most 90 uses, at most 100 uses, at most 200 uses, at most 300 uses, at most 400 uses, at most 500 uses, at most 600 uses, at most 700 uses, at most 800 uses, at most 900 uses, or at most 1,000 uses.

In some embodiments, the one or more light sources may be configured to function as strobe lights that are synchronized with image acquisition, and the image sensor chip is configured to acquire images on a fast timescale using a short exposure time to "freeze" motion of objects (e.g., sperm cells) within the sample. In these embodiments, the image sensor may be configured to capture images using an exposure time of less than 100 msec, less than 75 msec, less than 50 msec, less than 40 msec, less than 30 msec, less than 20 msec, less than 10 msec, less than 5 msec, or less than 1 msec.

Image Sensors:

In some embodiments, the imaging system may comprise a single image sensor. In some embodiments, the imaging system may comprise one additional image sensor, two additional image sensors, three additional image sensors, four additional image sensors, or five additional image sensors. Any of a variety of image sensors (or image sensor chips) known to those of skill in the art may be used in constructing the imaging system. Examples include, but are not limited to, charge-coupled device (CCD) image sensors, complementary metal-oxide-semiconductor (CMOS) image sensors, or any combination thereof. In some embodiments, the imaging system may comprise monochrome image sensors, color image sensors, or any combination thereof. In a preferred embodiment, a smart phone camera may be used as the image sensor. In another preferred embodiment, the smart phone may also provide the processor used for image acquisition, storage, and initial processing, as will be discussed in more detail below.

Image sensors suitable for use with the disclosed methods, devices, and systems may vary in terms of the image sensor pixel array format, the total number of image pixels contained within the image sensor chip, and the individual pixel size. For example, in some embodiments the image sensor pixel array format (number of horizontal pixels× number of vertical pixels) may be 640×480, 1280×1024, 1600×1200, 2560×2048, 4096×4096, etc. In some embodiments the image sensor pixel array may comprise a total pixel count of at least 0.1 megapixels, at least 0.5 megapixels, at least 1 megapixel, at least 2 megapixels, at least 3 megapixels, at least 4 megapixels, at least 5 megapixels, least 10 megapixels, at least 20 megapixels, at least 30 megapixels, at least 40 megapixels, at least 50 megapixels, at least 100 mega pixels, or more. Those of skill in the art will recognize that the sensor pixel array may have any value within this range, e.g., about 12 megapixel. In some embodiments, the size of individual pixels within the image sensor chip may be less than 10 microns, less than 5 microns, less than 4 microns, less than 3 microns, less than 2 microns, less than 1 micron, less than 0.5 microns, or less than 0.1 microns. Those of skill in the art will recognize that the size of the individual pixels may have any value within this range, e.g., about 1.55 µm.

In some embodiments, the image sensor may be configured to capture images with an adjustable exposure time. For example, in some embodiments the exposure time may range from about 0.001 msec to about 1 sec. In some embodiments, the image exposure time may be at least 0.001 msec, at least 0.01 msec, at least 0.1 msec, at least 1 msec, at least 10 msec, at least 100 msec, or at least 1 sec. In some embodiments, the image exposure time may be at most 1 sec, at most 100 msec, at most 10 msec, at most 1 msec, at most 0.1 msec, at most 0.01 msec, or at most 0.001 msec. Any of the lower and upper values described in this paragraph may be combined to form a range included within the present disclosure, for example, the image exposure time may range from about 0.1 msec to about 100 msec. Those of skill in the art will recognize that the image exposure time may have any value within this range, e.g., about 85 msec.

In some embodiments, the image sensor may be configured to capture single images. In some embodiments, the image sensor may be configured to capture a series of one or more images. In some embodiments, the series of images may comprise at least 1 image, at least 2 images, at least 3 images, at least 4 images, at least 5 images, at least 10 images, at least 50 images, at least 100 images, at least 500 images, at least 1,000 images, or more. In some embodiments, the image sensor may be configured to capture a series of images (e.g., video data) at a frame rate of at least 5 fps, at least 10 fps, at least 20 fps, at least 30 fps, at least 40 fps, at least 50 fps, at least 60 fps, at least 70 fps, at least 80 fps, at least 90 fps, or at least 100 fps.

In some embodiments, the image sensor may be configured to capture high speed images or a series of high speed images, e.g., using very short image exposure times and fast data acquisition rates in order to "freeze" the motion of objects (e.g., sperm cells) within the sample. In some embodiments, the image capture process may be synchronized with flashes of illumination light provided by a light source that has been configured to operate as a strobe light.

In these embodiments, the image sensor may be configured to capture images using an exposure time of less than 100 msec, less than 75 msec, less than 50 msec, less than 40 msec, less than 30 msec, less than 20 msec, less than 10 msec, less than 5 msec, or less than 1 msec.

Smart Phone Camera as Image Sensor:

As noted above, in a preferred embodiment of the disclosed methods, devices, and systems, the image sensor may be provided by a smart phone camera that comprises both the image sensor and optical components used for focusing. FIG. 7 provides one non-limiting example of an optical design wherein a smart phone camera is used with the disclosed sample-containing devices for imaging a sample. The smart phone is positioned relative to the optical assembly such that the camera is optically aligned with the micro lens, sample chamber, and light source. Any of a variety of commercially-available smart phones may be used including, but not limited to, iPhones, Samsung Galaxy phones, LG phones, Motorola phone, Nokia phones, etc. Representative examples of smart phone camera specifications are summarized in Table 1.

TABLE 1

Smart phone camera specifications
(data taken from www.phonearena.com).

|  | HTC 10 | iPhone 6s Plus | Samsung Galaxy S7 | LG G5 |
| --- | --- | --- | --- | --- |
| Resolution | 12 megapixel | 12 megapixel | 12 megapixel | 16 megapixel |
| Aspect Ratio (array format) | 4,000 × 3,000 pixels | 4032 × 3024 pixels | 4032 × 3024 pixels | 5312 × 2988 pixels |
| Pixel Size | 1.55 μm | 1.22 μ | 1.4 μm | 1.12 μm |
| Focal Length | 26 mm | 29 mm | 26 mm | 28 mm |
| F-Number | F 1.8 | F 2.2 | F 1.7 | F 1.8 |
| Focus | Laser AF | Phase detection AF | Dual pixel AF | Laser AF |
| Stabilization | Optical stabilization | Optical stabilization | Optical stabilization | Optical stabilization |

In some embodiments, a housing that encloses all or a portion of the imaging system, e.g., the illumination sub-assembly, may comprise one or more additional alignment features for the purpose of facilitating the alignment of a smart phone with the micro lens, sample chamber, and light source. In some embodiments, different models of the housing may be provided with alignment features that are tailored to mate with a specific model of smart phone.

Imaging Performance:

The imaging performance of the optical imaging system will be determined by the type, number, and arrangement of optical components used in designing and constructing the imaging system. For example, to first approximation, the magnification of the image at the plane of the image sensor will be determined by the focal length of the micro lens, the distance between the sample plane and the mid-plane of the micro lens, and the distance between the mid-plane of the micro lens and the image sensor. The overall magnification achieved will be further impacted by the focal lengths and positions of any additional lenses situated between the micro lens and image sensor (see FIG. 7 and FIG. 9).

In general, the magnification of the sample image at the position of the image sensor due to the optical elements of the imaging system may range from about 1× to about 300×. In some embodiments, the magnification of the sample image at the position of the image sensor may be at least 1×, at least 2×, at least 3×, at least 4×, at least 5×, at least 6×, at least 7×, at least 8×, at least 9×, at least 10×, at least 100×, or at least 300×. In some embodiments, the magnification of the sample image at the position of the image sensor may be at most 300×, at most 100×, at most 10×, at most 9×, at most 8×, at most 7×, at most 6×, at most 5×, at most 4×, at most 3×, at most 2×, or at most 1×. Any of the lower and upper values described in this paragraph may be combined to form a range included within the present disclosure, for example, the magnification of the sample image at the position of the image sensor may range from about 2× to about 6×. Those of skill in the art will recognize that the magnification of the sample image at the position of the image sensor may have any value within this range, e.g., about 5.5×.

In some embodiments, the optical magnification of the imaging system may be enhanced or replaced through the use of digital zoom techniques, i.e., by cropping an image down to a centered area with the same or a different aspect ratio as the original image, followed by interpolating the result back up to the same pixel dimensions as the original. In general, the magnification achieved through the use of digital zoom techniques may range from about 1× to about 10×. In some embodiments, the magnification achieved through the use of digital zoom techniques may be at least 1×, at least 2×, at least 3×, at least 4×, at least 5×, at least 6×, at least 7×, at least 8×, at least 9×, or at least 10×. In some embodiments, the magnification achieved through the use of digital zoom techniques may be at most 10×, at most 9×, at most 8×, at most 7×, at most 6×, at most 5×, at most 4×, at most 3×, at most 2×, or at most 1×. Any of the lower and upper values described in this paragraph may be combined to form a range included within the present disclosure, for example, the magnification achieved through the use of digital zoom techniques may range from about 3× to about 8×. Those of skill in the art will recognize that the magnification achieved through the use of digital zoom techniques may have any value within this range, e.g., about 2.8×.

In some embodiments, the total magnification of the imaging system achieved through a combination of optical magnification and the use of digital zoom techniques may range from about 1× to about 600×. In some embodiments, the total magnification achieved may be at least 1×, at least 2×, at least 3×, at least 4×, at least 5×, at least 6×, at least 7×, at least 8×, at least 9×, at least 10×, at least 20×, at least 30×, at least 40×, at least 50×, at least 60×, at least 70×, at least 80×, at least 90×, at least 100×, at least 200×, at least 300×, at least 400×, at least 500×, or at least 600×. In some embodiments, the total magnification achieved may be at most 600×, at most 500×, at most 400×, at most 300×, at most 200×, at most 100×, at most 90×, at most 80×, at most 70×, at most 60×, at most 50×, at most 40×, at most 30×, at most 20×, at most 10×, at most 9×, at most 8×, at most 7×, at most 6×, at most 5×, at most 4×, at most 3×, at most 2×, or at most 1×. Any of the lower and upper values described in this paragraph may be combined to form a range included within the present disclosure, for example, the total magnification achieved may range from about 10× to about 100×. Those of skill in the art will recognize that the total magnification achieved may have any value within this range, e.g., about 65×.

The field-of-view (i.e., the diameter or width of the sample region that is visible in the image) will be determined by the overall magnification of the image at the plane of the image sensor and the physical size of the image sensor. In general, the field-of-view in the disclosed imaging assemblies may range from about 0.1 mm to about 5 mm. In some embodiments, the field-of-view may be at least 0.1 mm, at least 0.2 mm, at least 0.3 mm, at least 0.4 mm, at least 0.5 mm, at least 1 mm, at least 1.5 mm, at least 2.0 mm, at least 2.5 mm, at least 3.0 mm, at least 3.5 mm, at least 4.0 mm, at least 4.5 mm, or at least 5.0 mm. In some embodiments, the field-of-view may be at most 5.0 mm, at most 4.5 mm, at most 4.0 mm, at most 3.5 mm, at most 3.0 mm, at most 2.5 mm, at most 2.0 mm, at most 1.5 mm, at most 1.0 mm, at most 0.5 mm, at most 0.4 mm, at most 0.3 mm, at most 0.2 mm, or at most 0.1 mm. Any of the lower and upper values described in this paragraph may be combined to form a range included within the present disclosure, for example, the field-of-view may range from about 0.5 mm to about 2.5 mm. Those of skill in the art will recognize that the field-of-view may have any value within this range, e.g., about 2.2 mm. In some embodiments, the field-of-view may be substantially rectangular, and may be specified by any pair of dimensions within the range of values indicated in this paragraph, e.g., about 215 μm×about 285 μm.

The depth-of-field (i.e., the vertical distance between the nearest and farthest objects in the sample that appear acceptably sharp in the image) will be determined (to first approximation) by the numerical aperture of the micro lens and overall magnification of the imaging system, with higher numerical apertures and magnifications corresponding to shallower depths-of-field. In some embodiments, it may be advantageous to adjust the numerical aperture of the micro lens so that the depth-of-field is approximately the same as the depth of the sample chamber. In some embodiments, it may be advantageous to adjust the depth of the sample chamber so that it is approximately the same as the depth-of-field. In some embodiments, the effective numerical aperture of the micro lens may be limited by the diameter of the micro lens itself. In some embodiments, the effective numerical aperture may be adjusted by placement of an aperture or field stop (e.g., adjacent to the micro lens, or adjacent to the image sensor) to limit the maximal entrance angle for light rays that pass through the micro lens and are focused onto the image sensor. In some embodiments, all or a portion of the second component of the sample-containing device (i.e., the lens holder that forms the lid of the sample chamber) may be fabricated from an optically opaque material and may form the aperture that determines the effective numerical aperture of the micro lens.

In general, the depth-of-field of the disclosed imaging assemblies may range from about 1 μm to about 50 μm. In some embodiments, the depth-of-field may be at least 1 μm, at least 5 μm, at least 10 μm, at least 20 μm, at least 30 μm, at least 40 μm, or at least 50 μm. In some embodiments, the depth-of-field may be at most 50 μm, at most 40 μm, at most 30 μm, at most 20 μm, at most 10 μm, at most 5 μm, or at most 1 μm. Any of the lower and upper values described in this paragraph may be combined to form a range included within the present disclosure, for example, the depth-of-field may range from about 20 μm to about 40 μm. Those of skill in the art will recognize that the depth-of-field may have any value within this range, e.g., about 14 μm.

The image resolution (i.e., the spatial resolution or minimum lateral separation distance, R, at which two points in the sample can be distinguished) is determined (to first approximation) by the numerical aperture of the micro lens and the wavelength of light being used to image the sample (as well as the refractive index of the sample), where higher numerical apertures and shorter wavelengths of light correspond to smaller minimum separation distances and higher spatial resolution images. In some cases, the spatial resolution of the image may be limited by the size of the pixels in the image sensor chip rather than the diffraction limit of the optical design.

In general, the image resolution for the disclosed imaging assemblies may range from about 0.5 μm to about 5 μm. In some embodiments, the image resolution may be at least 0.5 μm, at least 1.0 μm, at least 1.5 μm, at least 2.0 μm, at least 2.5 μm, at least 3.0 μm, at least 3.5 μm, at least 4.0 μm, at least 4.5 μm, or at least 5.0 μm. In some embodiments, the image resolution may be at most 5.0 μm, at most 4.5 μm, at most 4.0 μm, at most 3.5 μm, at most 3.0 μm, at most 2.5 μm, at most 2.0 μm, at most 1.5 μm, at most 1.0 μm, or at most 0.5 μm. Any of the lower and upper values described in this paragraph may be combined to form a range included within the present disclosure, for example, the image resolution may range from about 1.5 μm to about 2.5 μm. Those of skill in the art will recognize that the image resolution may have any value within this range, e.g., about 0.8 μm.

Imaging Modes and Wavelength Ranges:

A variety of imaging modes and wavelength ranges may be used in designing and implementing the methods, devices, and systems of the present disclosure. For example, the imaging system may be designed to capture greyscale and/or red-green-blue (RGB, or color) images. In some embodiments, the imaging system may be designed to operate in a bright-field imaging mode. In some cases, the sperm or other motile cells, bacteria, or single-cell microorganisms to be imaged may be poorly visible when using bright-field imaging, and an alternative imaging mode such as dark-field, phase contrast, or fluorescence imaging may be used. In some embodiments, the imaging system may incorporate one or more optical filters positioned between the micro lens and the cell phone lens, or between the micro lens and another lens in the optical path between the micro lens and the image sensor, for use in facilitating differential interference contrast imaging. In some embodiments, the imaging system may comprise an epi-illumination design so that excitation light used to excite a fluorescently-stained sample and the resultant emitted fluorescence are both transmitted through the micro lens and share a common optical path for a portion of their respective paths. In some embodiments, the micro lens itself, by virtue of the optical properties of the material of which it is fabricated, or of those for one or more optical coatings applied to one or more micro lens surfaces, may serve as an optical filter which selectively blocks transmission of light in one or more regions of the electromagnetic spectrum and selectively transmits light in one or more different regions of the electromagnetic spectrum.

Any of a variety of wavelength ranges known to those of skill in the art may be used to perform imaging with the disclosed imaging systems. For example, broad band visible light (or white light) may be used when imaging in bright-field, dark-field, or phase contrast mode. In some embodiments, broad band light, e.g., near-UV (about 310 nm to about 400 nm), visible (about 390 nm to about 700 nm), near-IR light (about 700 nm to about 2500 nm), or any spectral sub-region or combination thereof, may be used in any of these imaging modes (and at least one surface of the sample will be optically transparent in the corresponding wavelength range). In some embodiments, narrow band light may be used for exciting a sample, e.g., a fluorescently stained sample, and/or for imaging a sample. In some embodiments, it may be useful to stain the sample to be imaged using a dye molecule, contrast agent, or fluorophore to enhance the visibility of objects within the sample. In some cases, e.g., when using fluorescence as the imaging mode, the imaging system may incorporate a light source and/or optical filters and dichroic reflectors that provide illumination of the sample within a first specified wavelength range, and that collect light emitted by the sample within a second specified wavelength range for imaging, where the second specified wavelength range is different from the first specific wavelength range. Examples of commonly used fluorophores and preferred excitation/emission wavelengths include, but are not limited to, coumarin (387 nm/470 nm), fluorescein (494 nm/512 nm), Cy3 (554 nm/568 nm), alexa-fluor 555 (555 nm/580 nm), Texas Red (596 nm/615 nm), C5 (649 nm/666 nm), and the like. Typically a wavelength range is used for both providing excitation light and collecting emission or imaging light, where the wavelength range is centered on the specified wavelength and the bandwidth is determined by the optical properties of the light source, optical filters, and or dichroic reflectors incorporated into the imaging system. In some embodiments, the bandwidth of the light used for excitation and/or emission or imaging may be at least 5 nm, at least 10 nm, at least 25 nm, at least, at least 50 nm, at least 75 nm, at least 100 nm, or more.

Housing:

In general, the imaging systems of the present disclosure may comprise a housing which encloses the light source and any associated batteries, power supplies, or electronics (i.e., the illumination sub-assembly), all or a portion of the optical components, and, optionally, the image sensor. In a preferred embodiment, e.g., when a smart phone camera is used to provide the image sensor, the housing may not enclose the image sensor. In some embodiments, the housing may optionally further enclose a processor. In some embodiment, e.g., where a smart phone camera is used to provide the image sensor, the smart phone may optionally also provide the processor for controlling image acquisition, storage, and all or a portion of downstream image processing, as will be discussed in more detail below. In some embodiments, the housing may be configured to provide storage for one or more disposable sample-containing device such as those described above. In some embodiments, e.g., wherein the image sensor chip and processor of the imaging system are provided by a smart phone, the housing may comprise an alignment feature or adjustable fixture that facilitates optical alignment of the image sensor chip of the smart phone with the micro lens, sample chamber, and light source. The alignment feature and/or adjustable fixture may be integrated directly with the housing, or may be attached to the housing using fasteners or an adhesive.

Figure 10:
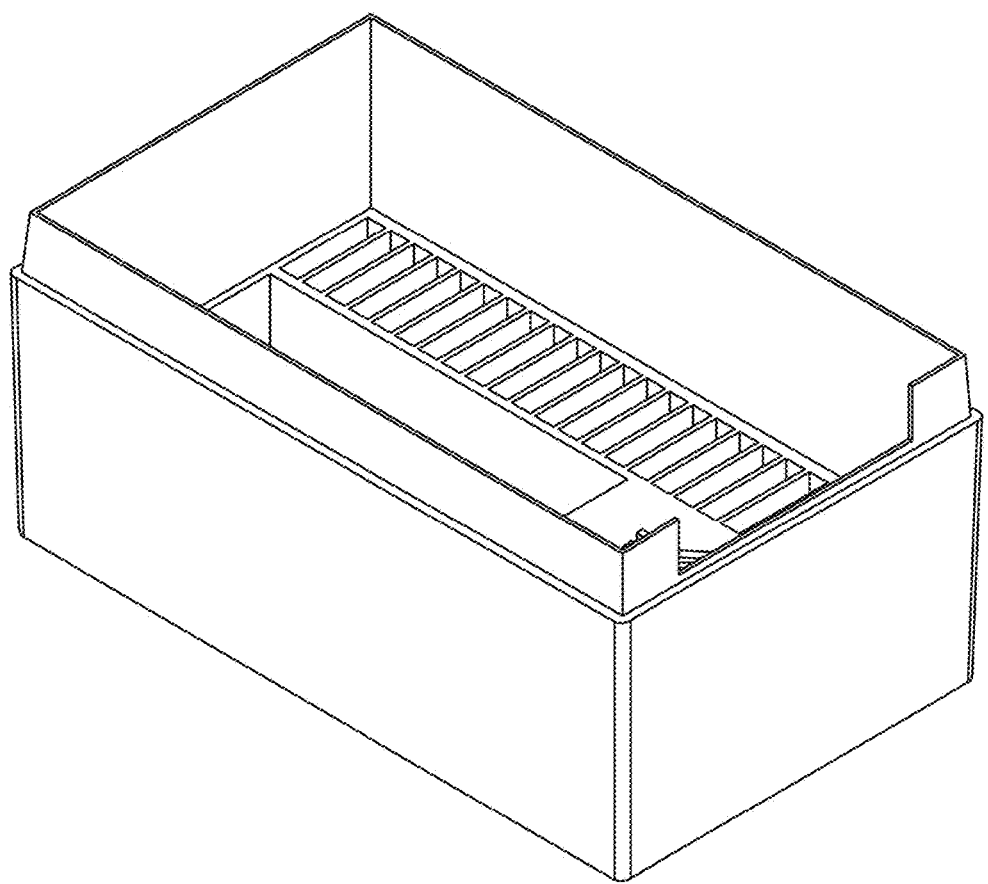
FIG. 10 provides an isometric drawing illustrating one non-limiting example of the lower component of an illumination sub-assembly housing for a compact imaging system used with devices such as the one illustrated in FIG. 2, where the lower component of the housing is separable from an upper component of the housing and incorporates storage space for a plurality of disposable devices such as the one illustrated in FIG. 2. Dimensions are in millimeters.
Figure 11:
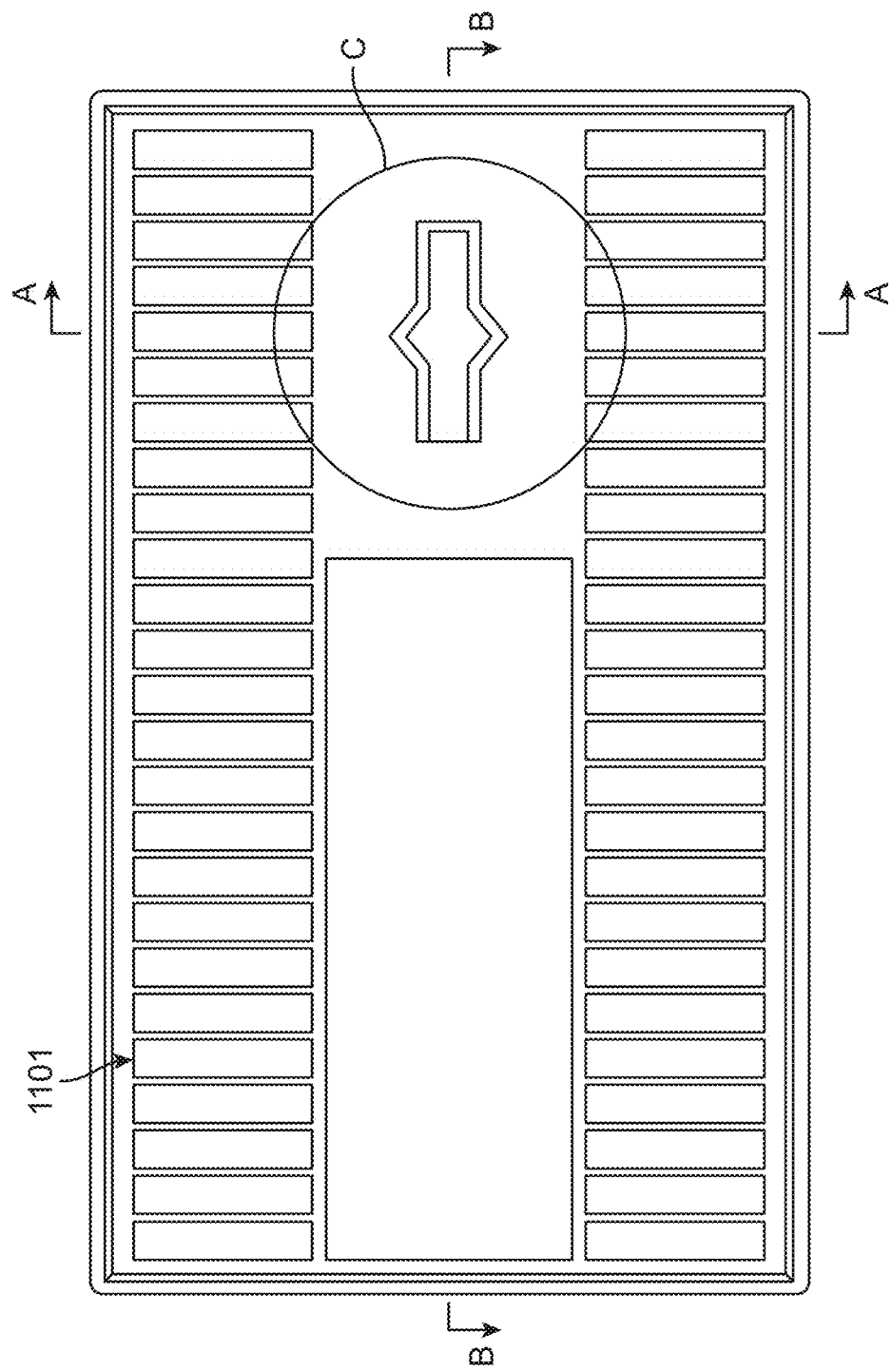
FIG. 11 provides a mechanical drawing (top view) illustrating one non-limiting example of the lower component of an illumination sub-assembly housing for a compact imaging system used with devices such as the one illustrated in FIG. 2. Dimensions are in millimeters.
Figure 12:
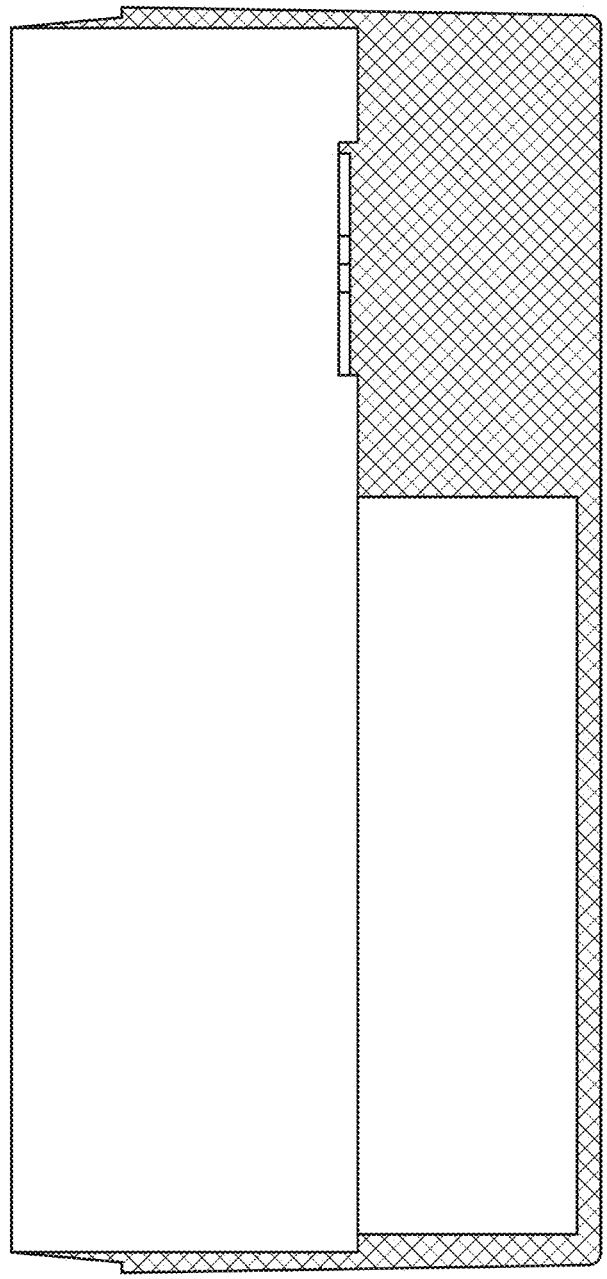
FIG. 12 provides a mechanical drawing (lengthwise cross-sectional view) illustrating one non-limiting example of the lower component of an illumination sub-assembly housing for a compact imaging system used with devices such as the one illustrated in FIG. 2. Dimensions are in millimeters.
Figure 13:
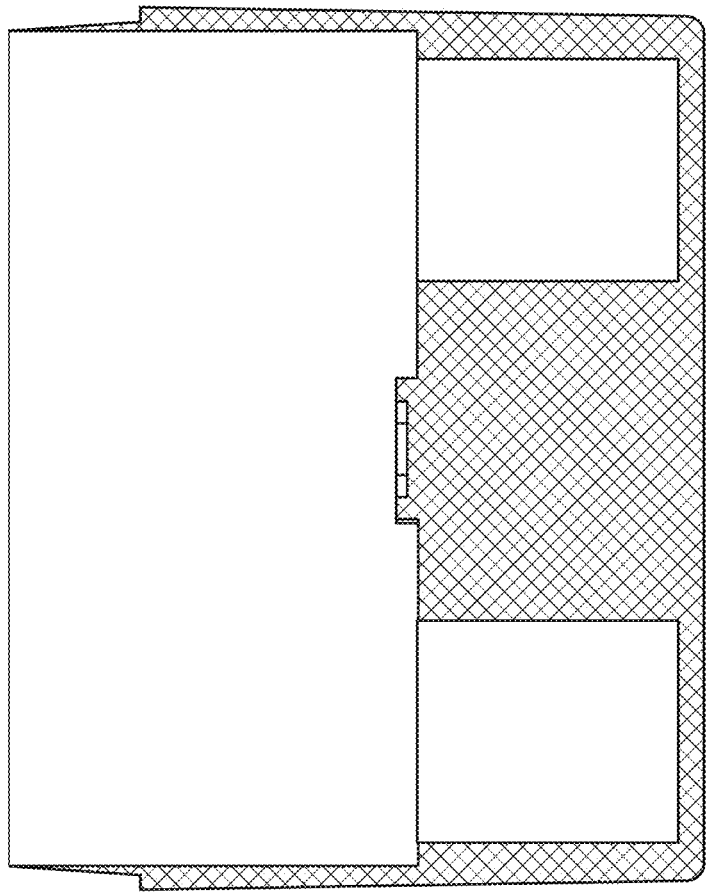
FIG. 13 provides a mechanical drawing (crosswise cross-sectional view) illustrating one non-limiting example of the lower component of an illumination sub-assembly housing for a compact imaging system used with devices such as the one illustrated in FIG. 2. Dimensions are in millimeters.
Figure 14:
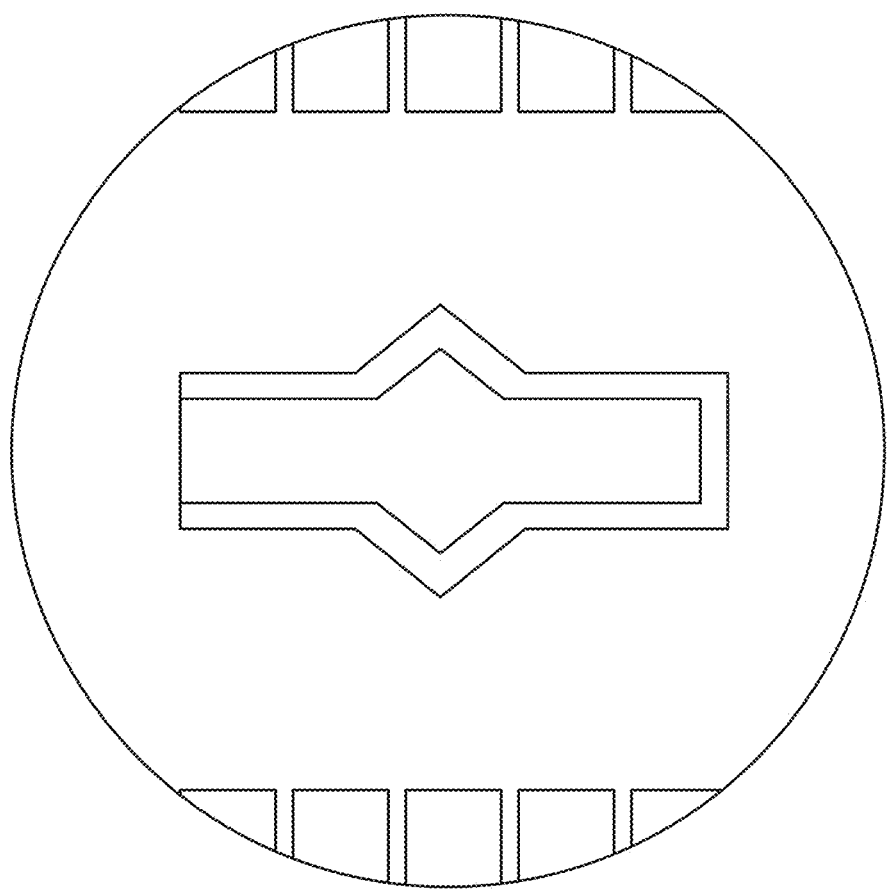
FIG. 14 provides a detail view of a feature on the top side of an internal surface of the housing shown in FIG. 11. Dimensions are in millimeters.

FIG. 10 provides an isometric drawing illustrating one non-limiting example of the lower component of an imaging system housing, where the lower component of the housing is separable from an upper component of the housing and incorporates storage space for a plurality of disposable sample-containing devices such as those illustrated in FIG. 2. In some embodiments, the separable upper and lower components may include a feature, e.g., a catch or "click-in-place" feature that secures them when joined and ensures a fixed, repeatable relative position. FIG. 11 provides a mechanical drawing (top view) of the same housing component that illustrates storage features 1101 (e.g., slots) used to store one or more disposable sample-containing devices. There are 50 storage features illustrated in FIG. 11, but as will be readily apparent to one of skill in the art, the housing may be configured for storage of any number of sample-containing devices provided that the dimensions and space requirements for the specified number of devices are compatible with the dimensions of the housing. FIG. 14 provides a detail view of a feature of the housing component illustrated in FIG. 11. Specifically, FIG. 14 shows one non-limiting example of an opening or optically-transparent window in the lower housing component, where the opening or optically-transparent window is aligned with the sample-containing device when the latter is positioned in or on the imaging system, and where the opening or optically-transparent window has a geometry that corresponds to the geometry of the sample chamber within the sample-containing device. The light source (not shown in FIG. 11 or FIG. 14) is positioned below the opening or optically-transparent window. FIG. 12 provides a mechanical drawing (lengthwise cross-sectional view) illustrating the housing component shown in FIG. 11. The hatched area at the lower right corner in this view depicts the portion of the housing that forms an enclosure for the light source, battery or power supply, and associated electronics. FIG. 13 provides a mechanical drawing (crosswise cross-sectional view) illustrating the housing component shown in FIG. 11. The hatched area in the lower center region in this view again depicts the portion of the housing that forma an enclosure for the light source, battery or power supply, and associated electronics, with the storage space for disposable sample-containing devices positioned on either side of the light source enclosure.

Figure 15:
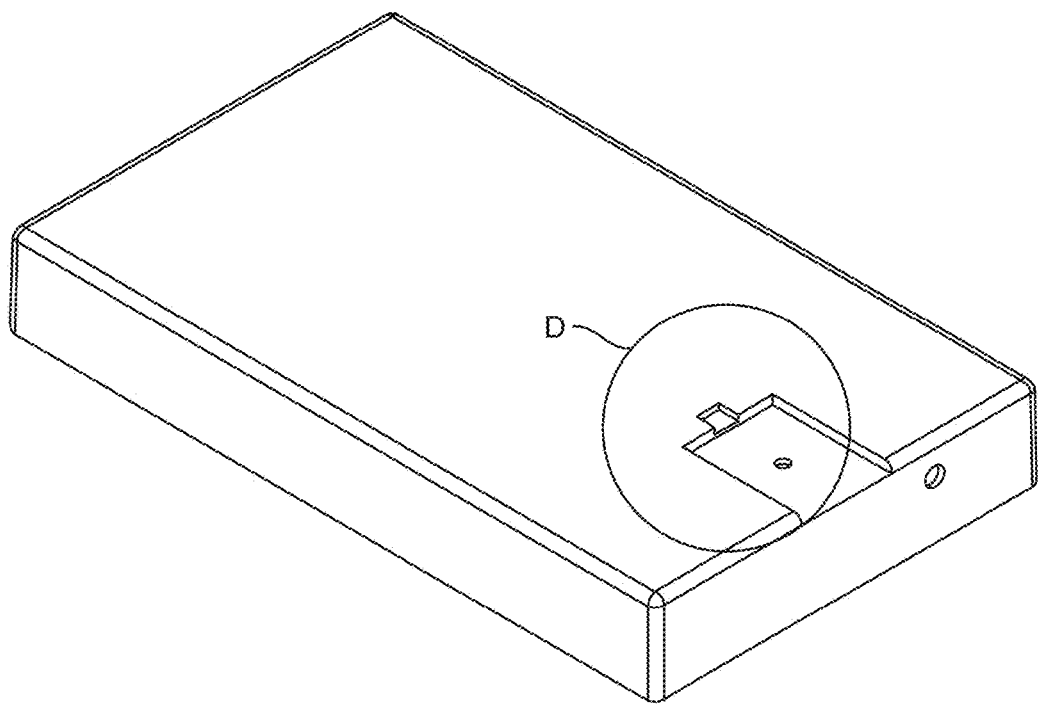
FIG. 15 provides an isometric drawing illustrating one non-limiting example of the upper component of an illumination sub-assembly housing for a compact imaging system used with devices such as the one illustrated in FIG. 2.
Figure 16:
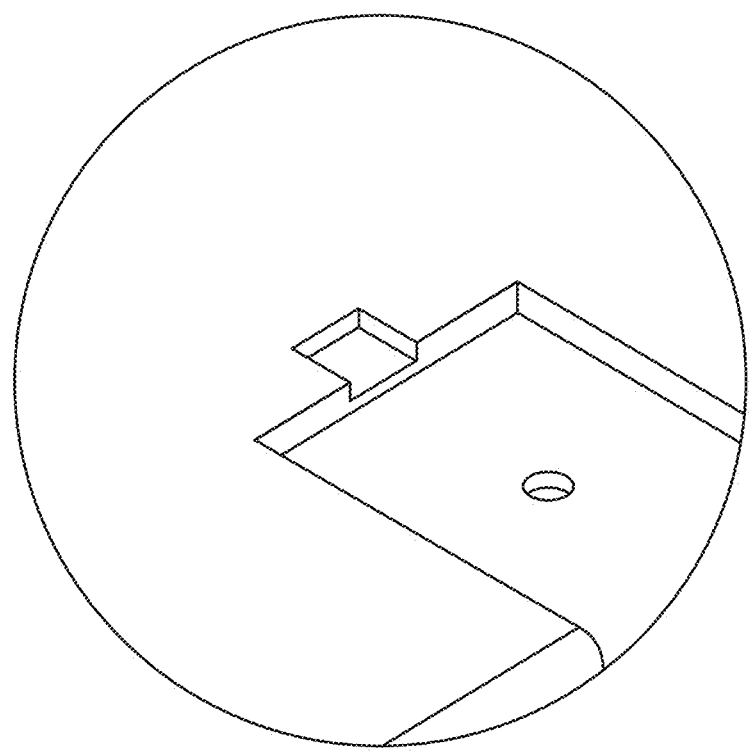
FIG. 16 provides a detail view of a feature on the top side of the upper component of the housing shown in FIG. 15.
Figure 17:
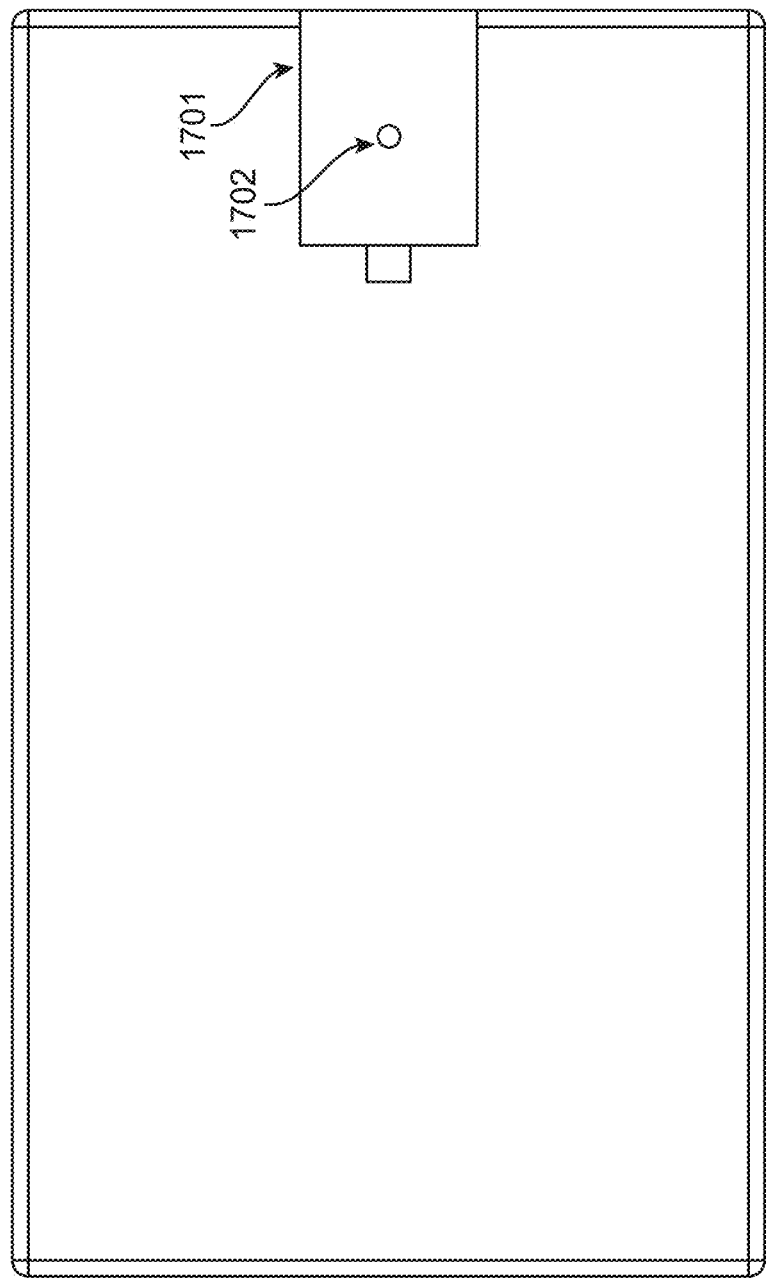
FIG. 17 provides a mechanical drawing (top view) illustrating one non-limiting example of the upper component of an illumination sub-assembly housing for a compact imaging system used with devices such as the one illustrated in FIG. 2. Dimensions are in millimeters.
Figure 18:
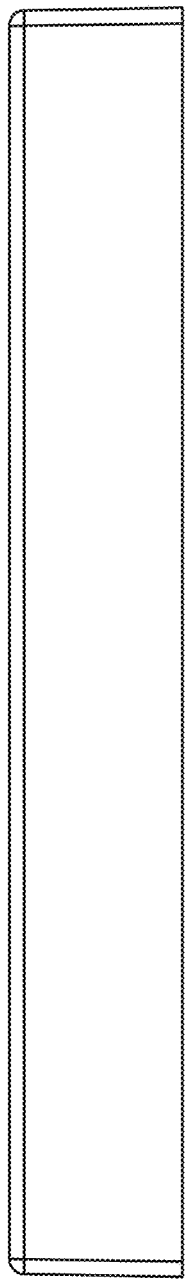
FIG. 18 provides a mechanical drawing (side view) illustrating one non-limiting example of the upper component of an illumination sub-assembly housing for a compact imaging system used with devices such as the one illustrated in FIG. 2. Dimensions are in millimeters.
Figure 19:
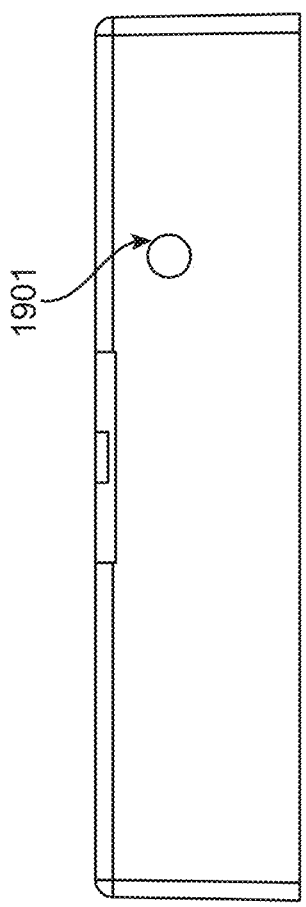
FIG. 19 provides a mechanical drawing (end view) illustrating one non-limiting example of the upper component of an illumination sub-assembly housing for a compact imaging system used with devices such as the one illustrated in FIG. 2. Dimensions are in millimeters.

FIG. 15 provides an isometric drawing illustrating one non-limiting example of the upper component of an imaging system housing for the compact imaging system used with devices such as the one illustrated in FIG. 2. The upper component mates with the lower component to form an enclosure for the light source, and optionally for the image sensor and/or other optical components of the imaging system. FIG. 16 shows a detail view of an alignment feature and illumination opening (or transparent window) on the upper component of the housing. The alignment feature is used to position a sample-containing device with respect to the imaging system so that the sample chamber contained therein is in optical alignment with the light source, micro lens, and image sensor. The opening or window in the upper housing component allows the light provided by the light source to pass through the optically-transparent sample chamber of the sample-containing device. FIG. 17, FIG. 18, and FIG. 19 provide mechanical drawings (top view, side view, and end view, respectively) of the upper housing component. The alignment feature 1701 used to position the sample-containing device relative to the imaging system and the opening or window 1702 through which illumination light impinges upon the sample chamber of the device are indicated in FIG. 17. In some embodiments, the illumination sub-assembly housing may comprise an opening (1901) for a switch that is used to turn the light source on and off, as illustrated in FIG. 19. In some embodiments, the user may push the switch to turn the light source on and to turn it off. In some embodiments, the user may push the switch once to turn the light source on for a specified period of time during which an image or series of images of the sample are acquired. In some embodiments, the light source may be automatically controlled by a processor that also controls the image acquisition process.

Figure 20:
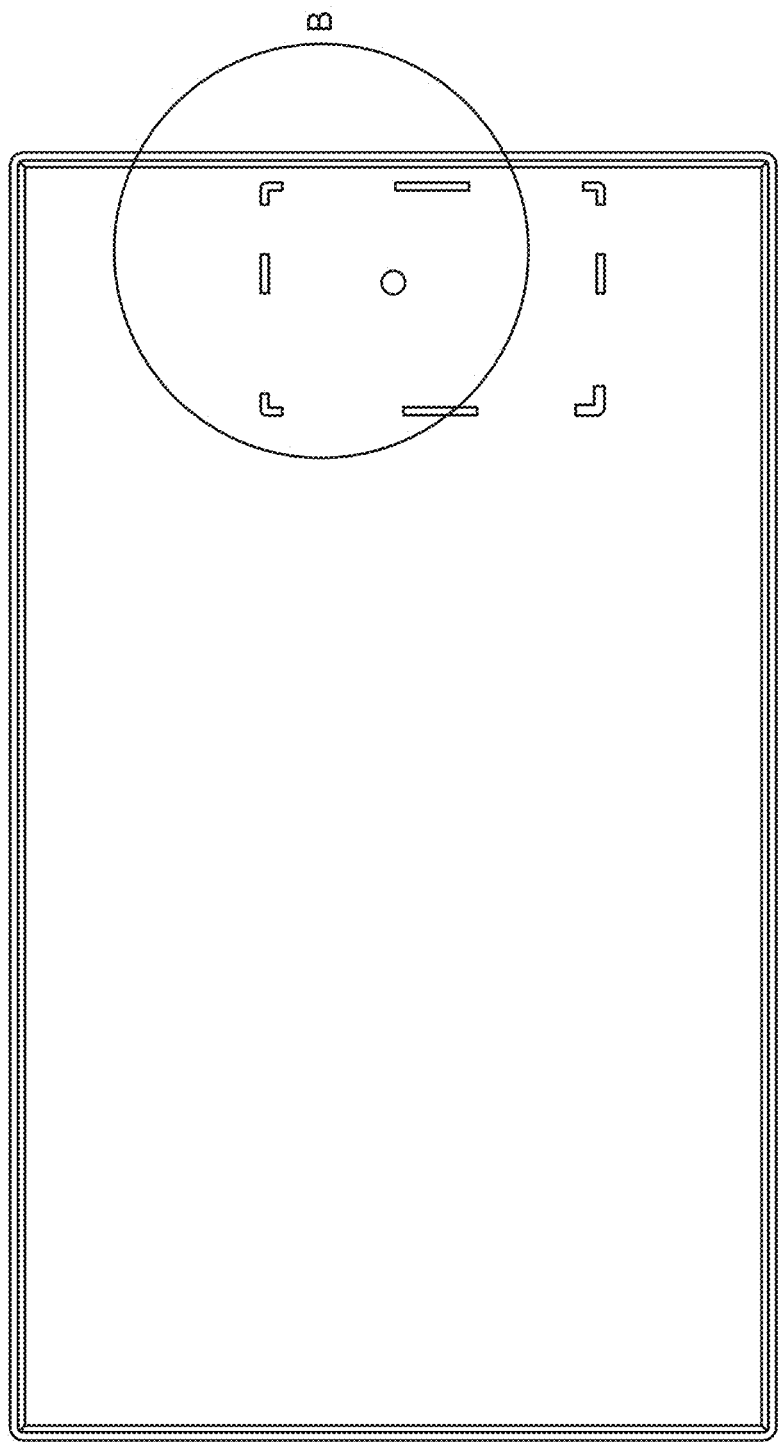
FIG. 20 provides a mechanical drawing (bottom view) illustrating one non-limiting example of the upper component of an illumination sub-assembly housing for a compact imaging system used with devices such as the one illustrated in FIG. 2. Dimensions are in millimeters.
Figure 21:
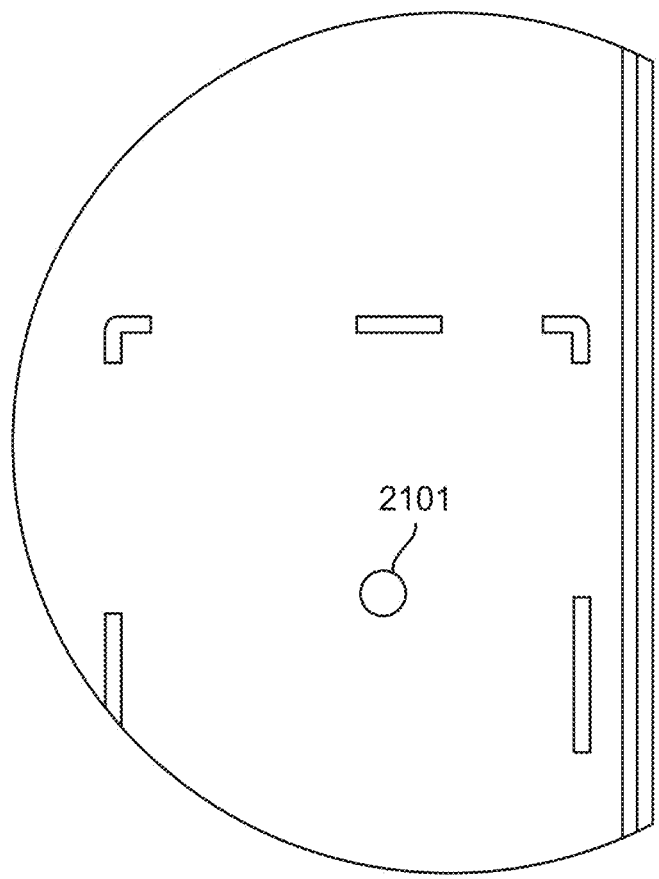
FIG. 21 provides a detail view of a feature on the bottom (internal) side of the upper component of the housing shown in FIG. 17. Dimensions are in millimeters.

FIG. 20 and FIG. 21 provide mechanical drawings (a bottom view and a detail view respectively) of the underside of the upper housing component that illustrate alignment features for ensuring that the light source (or light source sub-assembly) is properly aligned with respect to the housing. An opening or window 2101 in the housing (FIG. 21) allows light from the light source to pass through the sample chamber of a sample-containing device.

In general, the housing may comprise one, two, or three or more components, wherein in some embodiments, two or more of the housing components may be separable to allow convenient access to the interior of the housing, e.g., as when the housing is further configured to provide storage space for one or more sample-containing devices.

In general, the housing may be substantially rectangular or boxed shape (i.e., of a rectangular cuboid shape), but in some embodiments may have any of a variety of other geometries known to those of skill in the art. In general, a long dimension of the housing may range from about 5 cm to about 20 cm. In some embodiments, the longest dimension of the housing may be at least 5 cm, at least 6 cm, at least 7 cm, at least 8 cm, at least 9 cm, at least 10 cm, at least 15 cm, or at least 20 cm. In some embodiments, the longest dimension of the housing may be at most 20 cm, at most 15 cm, at most 10 cm, at most 9 cm, at most 8 cm, at most 7 cm, at most 6 cm, or at most 5 cm. Any of the lower and upper values described in this paragraph may be combined to form a range included within the present disclosure, for example, the longest dimension of the housing may range from about 7 cm to about 15 cm. Those of skill in the art will recognize that the longest dimension of the housing may have any value within this range, e.g., about 12.5 cm.

In some embodiments, the dimensions of the optical imaging system may be specified such that the total volume of the imaging system housing may range from about 125 $cm^3$ to about 8,000 $cm^3$. In some embodiments, the total volume of the housing may be at least 125 $cm^3$, at least 250 $cm^3$, at least 500 $cm^3$, at least 1,000 $cm^3$, at least 2,000 $cm^3$, at least 3,000 $cm^3$, at least 4,000 $cm^3$, at least 5,000 $cm^3$, at least 6,000 $cm^3$, at least 7,000 $cm^3$, or at least 8,000 $cm^3$. In some embodiments, the total volume of the housing may be at most 8,000 $cm^3$, at most 7,000 $cm^3$, at most 6,000 $cm^3$, at most 5,000 $cm^3$, at most 4,000 $cm^3$, at most 3,000 $cm^3$, at most 2,000 $cm^3$, at most 1,000 $cm^3$, at most 500 $cm^3$, at most 250 $cm^3$, at most 125 $cm^3$. Any of the lower and upper values described in this paragraph may be combined to form a range included within the present disclosure, for example, the total volume of the housing may range from about 500 $cm^3$ to about 2,000 $cm^3$. Those of skill in the art will recognize that the longest dimension of the housing may have any value within this range, e.g., about 1,300 $cm^3$.

In general, the housing may be fabricated from any of a variety of materials using any of a variety of fabrication methods known to those of skill in the art, where the choice of material typically depends on the choice of fabrication technique or vice versa. Examples of suitable materials include, but are not limited to, cardboard, plastic (e.g., acrylonitrile-butadiene-styrene (ABS)), sheet metal, aluminum, stainless steel, and the like. Examples of fabrication methods that may be used include, but are not limited to, injection molding, sheet metal-folding, CNC machining, 3D printing, and the like.

In some embodiments, the housing may be contained within an additional package, e.g., a foldable package or cover (e.g., a cardboard cover) that fits over the housing of the optical imaging system and that may further comprise company logos, product labeling information, etc.

Temperature Controller:

In some embodiments, the imaging system may further comprise a temperature controller and thermal interface features that are configured to maintain the sample chamber at a specified temperature. Examples of suitable temperature control elements include, but are not limited to, resistive heating elements, miniature infrared-emitting light sources, Peltier heating or cooling devices, heat sinks, thermistors, thermocouples, and the like. Thermal interface features will typically be fabricated from materials that are good thermal conductors (e.g. copper, gold, silver, etc.) and will typically comprise one or more flat surfaces capable of making good thermal contact with at least one surface of the sample chamber and/or external heating blocks or cooling blocks.

Processor(s):

In some embodiments, the optical imaging system may further comprise one or more processors, e.g. microprocessors. In some embodiments, the one or more processors may be integrated with the optical imaging system. In some embodiments, the one or more processors may be provided by a desk top computer, personal computer, laptop computer or tablet that is connected to the compact optical imaging system via a suitable data communication link, e.g., an RS-232 cable, USB cable, WiFi link, or blue tooth connection. In a preferred embodiment, the processor (as well as the image sensor) may be provided by a smart phone that is positioned on or within the optical imaging system so as to facilitate the capture of one or more images of a sample contained within a sample-containing device positioned on or within the optical imaging system. In some embodiments, the smart phone processor may also perform all or a portion of the image processing used to identify and track motile objects, e.g., sperm cells, over time and provide morphological and/or motility data about the sample.

Image Processing:

In some embodiments, image processing may be used to identify objects within a series of one or more images captured for a sample by the optical imaging system. In some embodiments, all or a portion of the image processing may be handled locally, e.g. by a processor that is integrated within the optical imaging system or by the processor of a smart phone used to capture the images of the sample. In some embodiments, the image processing may comprise a software application running on a local processor, e.g., that of a desktop computer or laptop, that provides control of video data acquisition, and optionally, image processing capability. In some embodiments, the image processing may comprise a smartphone application that provides control of video data acquisition, and optionally, image processing capability. In some embodiments, for example, the image processing software (e.g., a local software application, smartphone application, or a cloud-based application) may provide control of pixel binning and the resolution of video data captured by an image sensor or smartphone camera. In some embodiments, reducing the resolution of the video data to, e.g., 1,280 pixels wide×720 lines per frame, 640 pixels×480 pixels per frame, or 480 pixels wide×360 lines per frame may reduce the image processing time required to provide a motility analysis result. In some embodiments, the optical imaging system may be configured to upload the image data to an intranet- or internet-based database, and all or a portion of the image processing may be performed remotely, e.g., using an image processing workstation connected to the intranet- or internet-based database, or using cloud-based image processing software.

In some embodiments, the initial processing of the image data may comprise applying a contrast adjustment algorithm, a noise reduction algorithm, a flat-field or vignetting correction algorithm, an optical distortion correction algorithm, an optical aberration correction algorithm, a data compression algorithm, or any combination thereof to the series of one or more image(s) captured by the optical imaging system.

In some embodiments, further processing of the image data may be performed, and may comprise applying an edge detection algorithm, an image segmentation algorithm, a centroid calculation algorithm, a feature detection algorithm, a pattern detection algorithm, a motion tracking algorithm, a mathematical analysis algorithm, a statistical analysis algorithm, or any combination thereof to the series of one or more image(s) captured by the optical imaging system.

In some embodiments, the output of the image processing may comprise providing a test result having to do with a morphological and/or motility analysis of objects within the sample under analysis. For example, in the case of semen samples, the image processing output parameter (or test result) may comprise a total sperm count, a total sperm concentration, a motile sperm count, a motile sperm concentration, an average sperm motility or velocity, a sperm motility or velocity for the motile fraction, an identification of the presence of morphological defects, the number of morphological defects detected, or any combination thereof. In some embodiments, similar morphological and/or motility parameters may be provided for motile objects (e.g., bacteria, single-cell microorganisms, etc.) in other types of samples.

Applications/Methods of Use:

The disclosed devices and systems may be used in performing morphological and/or motility analysis for a variety of samples and applications. Examples of potential applications include, but are not limited to, diagnosis of farm animal and race horse reproductive issues, analysis of fresh or previously frozen semen samples at stud farms and farm animal breeding facilities that utilize artificial insemination techniques (e.g., to assess the quality of a semen sample and evaluate whether or not it should be used for artificial insemination), diagnosis of human male reproductive problems (particularly by physicians working in rural areas or small urban centers that currently lack access to a local, commercially-available CASA system), evaluation of the quality of a semen sample prior to use in a human in vitro fertilization procedure, detection of bacteria or other single cell microorganisms in water samples (for environmental monitoring), etc.

In some embodiments, the disclosed methods, devices, and systems may be used to provide a test result, e.g., a sperm morphology or motility result, which is used by a veterinarian to make a diagnostic and/or treatment decision for farm animals or race horses (i.e., an agricultural diagnostic and/or treatment decision). In some embodiments, the disclosed methods, devices, and systems may be used to provide a test result, e.g., a sperm morphology or motility result, which is used by a physician to make a diagnostic and/or treatment decision for humans (i.e., a clinical diagnostic and/or treatment decision). For example, in some embodiments, repeated measurements of the sperm count of a human or animal patient who is undergoing therapy based on a prescribed set of one or more drugs, e.g., antioxidants, may be used to determine if the patient is improving on a day-by-day or week-by-week basis. In some embodiments, one or more morphological and/or motility test results, e.g., a sperm morphology or motility result, may be stored in a cloud-based database, and may be used to identify a geographical distribution of human or animal male reproductive issues, and may further be used to make a marketing decision, e.g., a decision whereby a recommendation for the use of certain treatments or procedures is made according to the geographical location of the individual.

In some instances, the disclosed methods, devices and, systems may be used as a basic tool for biological research or as an educational toy, e.g., for imaging and studying bacteria, algae, yeast, cells, unicellular ciliates such a paramecium, small insects, and the like in samples collected from culture plates, ponds, sea water, rain water, rain drops, bodily fluids such as blood or plasma, etc. For example, a biological field scientist studying water quality issues and their impact on the environment may draw samples of pond water and place a drop in a sample imaging device of the present disclosure. The battery-operated, portable, compact imaging system of the present disclosure then may be used along with the scientist's smartphone to image organisms within the sample and determine such quantities as types of organisms present, number of each organism present, concentration of each organism present, motility data for motile organisms, morphology data for each type of organisms, etc. In some instances, the image and/or video data generated using the disclosed device and systems is automatically date-stamped, time-stamped, and geo-stamped. In some instances, the image processing software used to analyze motility and morphology may further comprise tools for identifying organisms and retrieving genus and species information, e.g., by connecting to a cloud-based database and using look-up tools and/or machine learning algorithms to compare images. In some instances, images and/or video data may be shared over the web using social networking tools such as YouTube, Instagram, or Facebook.

EXAMPLES

These examples are provided for illustrative purposes only and not to limit the scope of the claims provided herein.

Example 1—Use of a Sample Imaging Device and Compact Imaging System for Sperm Motility Analysis The disclosed sample imaging devices, compact imaging systems, and image processing software provide a convenient and portable means for performing sperm motility testing by veterinarians treating farm animal and race horse reproductive issues, by veterinarians and technicians working at stud farms and farm animal breeding facilities that utilize artificial insemination techniques, and by physicians treating male reproductive problems in rural areas or smaller urban centers.

Figure 22:
FIG. 22 illustrates one non-limiting example of a smartphone screen showing the presence of a SpermCell image acquisition and analysis application (2201) that uses the smartphone camera system to take video data of a sample placed in a sample imaging device such as that shown in FIG. 2.

The use of such as system is described as follows. Previously frozen semen samples are thawed and optionally diluted with an appropriate isotonic buffer solution. Fresh semen samples may be used directly with or without dilution depending on the type of sample. A droplet of the prepared semen sample is then placed on the sample chamber of the sample imaging device (FIG. 2, 201), and a lens holder is positioned using the alignment feature(s) of the device (FIG. 5), thereby bringing the micro lens into alignment and contact with or close proximity to the sample, and sealing the sample chamber (the large indented area surrounding the sample chamber 201 in FIG. 2 provides and overflow space for excess sample). The sample imaging device is then placed within the alignment feature of the compact imaging system housing (FIG. 6), thereby bringing the sample chamber into optical alignment with the light source, and the light source is turned on. In those embodiments where the camera of a smartphone is used to provide the imaging sub-assembly of the imaging system, a smartphone application stored on the phone is activated (FIG. 22, 2201), and patient and/or sample information may be scanned in (e.g., using barcodes) or manually entered. Examples of patient and/or sample information that may be entered include, but are not limited to, patient identification, sample identification, patient age, donor age (human or animal), sample preparation protocol used (if any), date, time, location, etc. The smartphone is then positioned using alignment features built into the housing of the compact imaging system so that the smartphone camera is optically aligned with the sample chamber of the device and the light source, and a series of video images of the sperm in the sample are captured.

Following capture of the video data, the data may be partially processed or completely processed locally (e.g. using the smartphone's processor), or the raw video data or data resulting from pre-processing of the images may be uploaded to an intranet- or internet-based system and processed remotely. In some cases, the image data may be processed using a cloud-based application and stored in a cloud-based database.

Figure 23A:
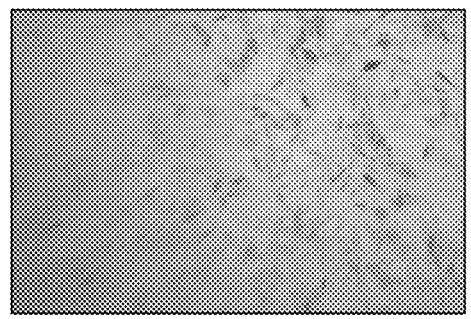
FIGS. 23A-B show examples of a greyscale image of sperm cells (FIG. 23A) and the same image after performing image processing to identify individual sperm cells in the image (FIG. 23B).
Figure 23B:
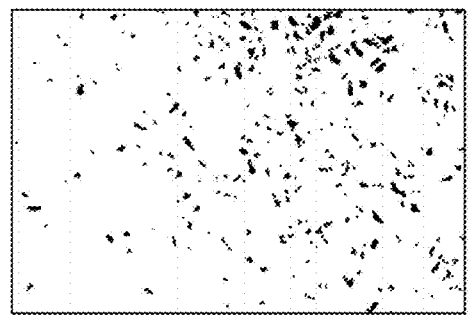
Figure 24:
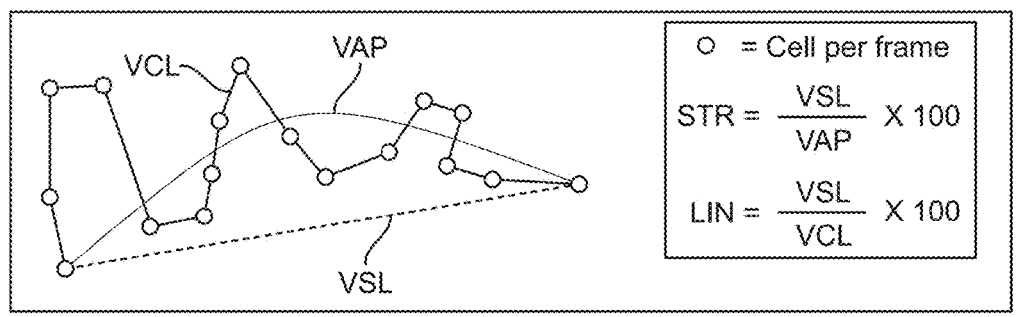
FIG. 24 illustrates the path followed by an individual sperm cell from one video image frame to the next, and calculations used to characterize sperm motility.

FIGS. 23A-B provide examples of a greyscale image of sperm cells (FIG. 23A) and the same image after performing image processing to identify individual sperm cells in the image (FIG. 23B). Once the individual cells have been identified in each video frame, they may be tracked from frame to frame (FIG. 24) to generate paths for which a variety of motility parameters may be calculated. Non-limiting examples of sperm motility parameters which may be calculated from the processed video data are listed in Table 1. The definition of different velocity parameters that may be calculated are illustrated in FIG. 24. Additional motility parameters such as path straightness (STR) and path linearity (LIN) may also be calculated.

TABLE 1

Examples of Sperm Motility Parameters

| Motility Parameter | Quantity or Units |
| --- | --- |
| Sperm concentration | sperm count per ml |
| Total motility | total number & percentage of motile sperm |
| | total number & percentage of immotile sperm |
| Velocity parameters: | micrometers/sec |
| Curvilinear velocity (VCL) | |
| Straight-line velocity (VSL) | |
| Average pathway velocity (VAP) | |
| Type of motility: | percent values |
| Progressive motility (A group) | |
| Curvilinear motility (B group) | |
| Non-progressive motility (C group) | |
| Immotile sperm (D group) | |

FIG. 25 provides one non-limiting example of a sperm motility analysis report that may be displayed on the screen of the smartphone running the video acquisition and processing application. In some embodiments, the video acquisition and processing application may further provide capability for assessing sperm morphology, identifying the presence of sperm morphological defects, determining the number of sperm morphological defects present (on an absolute count or percentage basis), etc.

Figure 26:
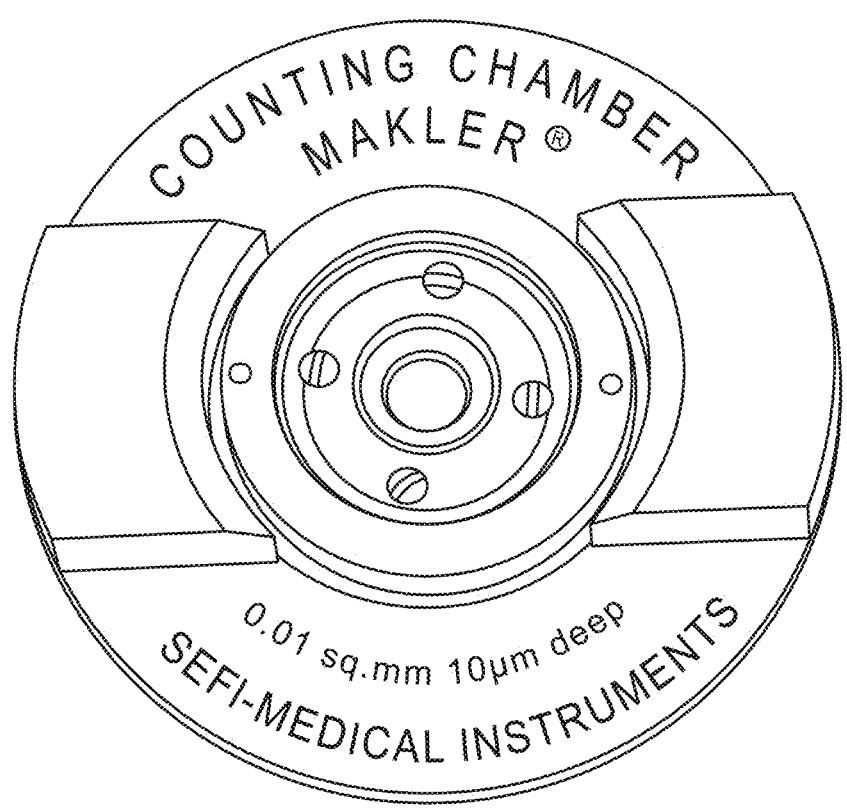
FIG. 26 shows an image of a Makler® counting chamber used for validation of SpermCell image processing and sperm motility analysis software.
Figure 27A:
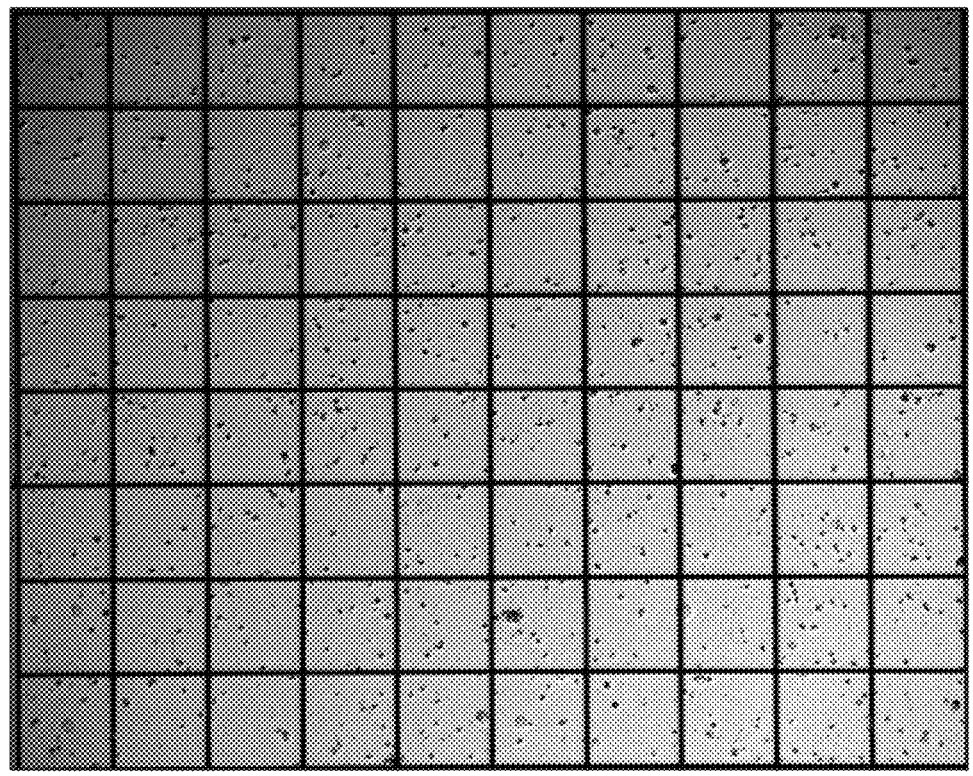
FIGS. 27A-B show examples of sperm cell images (FIG. 27A—low magnification.
Figure 27B:
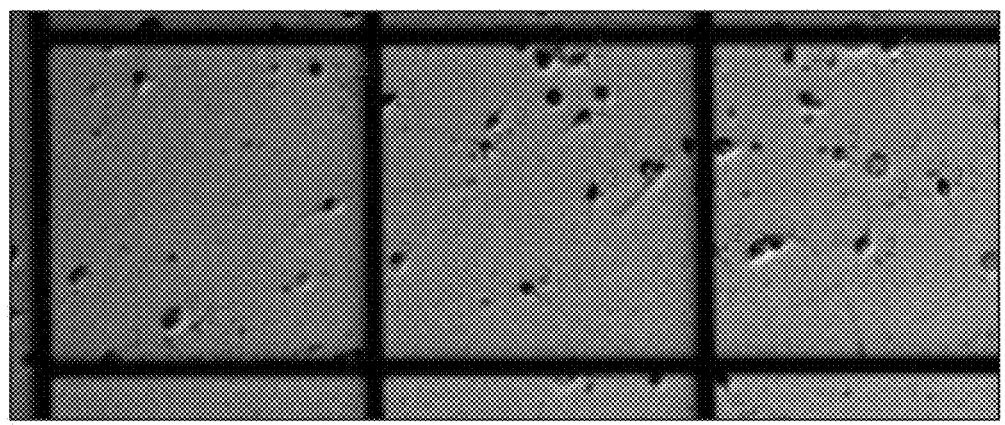

Example 2—Validation of SpermCell Image Processing and Sperm Motility Analysis Software FIG. 26 shows an image of a Makler® counting chamber (Sefi-Medical Instruments Ltd., distributed by Irvine Scientific, Santa Ana, Calif.), an industry standard device that is being used for validation of SpermCell image processing and sperm motility analysis software. Video images of sperm samples captured using a Makler® counting chamber (FIGS. 27A-B) were processed manually on a computer screen to validate the SpermCell image processing and analysis software running on a smartphone that was connected to the internet. An example of the results of the analysis are summarized in FIG. 28.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A device for imaging a sample, the device comprising:
    a) a substantially planar first component, wherein the first component comprises an alignment feature and a sample chamber configured to hold the sample to be imaged, and wherein at least one surface of the sample chamber is optically transparent; and
    b) a removable, substantially planar second component that forms a lid for the sample chamber and that comprises a micro lens, wherein the micro lens is optically aligned with the sample chamber and contacts the sample or is placed in close proximity to the sample when the removable second component is positioned in the alignment feature.

2. The device of claim 1, wherein the first component comprises two or more sample chambers.

3. The device of claim 1, wherein the micro lens is a ball lens, a cylindrical lens, or a rectangular lens.

4. The device of claim 3, wherein the micro lens is a ball lens and has a diameter of between about 0.5 mm and about 2 mm.

5. The device of claim 4, wherein the micro lens is fabricated from H-ZLaF71, LaSFN9, or S-LAH79.

6. The device of claim 1, wherein the sample chamber has a depth of between about 5 μm and about 20 μm.

7. The device of claim 1, wherein the first component or second component is fabricated from soda lime glass, borosilicate glass, fused silica, cyclic olefin copolymer (COC), cyclic olefin polymer (COP), poly(methyl methacrylate) (PMMA), Tyril™ 867E styrene and acrylonitrile (SAN) resin, or any combination thereof.

8. The device of claim 1, wherein the device is a single-use disposable.

9. A motility analysis system comprising:
    a) a sample-containing device comprising:
        i) a substantially planar first component, wherein the first component comprises a first alignment feature and a sample chamber configured to hold a sperm sample to be imaged, and wherein at least one surface of the sample chamber is optically transparent; and
        ii) a removable, substantially planar second component that forms a lid for the sample chamber and that comprises a micro lens, wherein the micro lens is optically aligned with the sample chamber and contacts the sperm sample or is placed in close proximity to the sperm sample when the removable second component is positioned in the first alignment feature; and
    b) an imaging system, wherein the imaging system comprises:
        i) a light source configured to direct light through the optically transparent surface of the sample chamber;

ii) an image sensor chip configured to acquire a series of one or more image(s) from light transmitted, scattered, or emitted by the sample and collected by the micro lens;
iii) a processor configured to perform initial processing and storage of image data for the series of one or more image(s) acquired by the image sensor chip; and
iv) a housing, wherein the housing comprises a second alignment feature and encloses the light source, and wherein the image sensor chip, micro lens, sample chamber, and light source are optically aligned when the device is positioned in the second alignment feature.

10. The motility analysis system of claim 9, wherein the first component comprises two or more sample chambers.

11. The motility analysis system of claim 9, wherein the housing does not enclose the image sensor chip, and wherein the housing comprises an upper component and a lower component that are separable, and wherein the lower component further comprises features configured for storage of one or more sample-containing devices.

12. The motility analysis system of claim 9, wherein the micro lens is a ball lens, a cylindrical lens, or a rectangular lens.

13. The motility analysis system of claim 12, wherein the micro lens is a ball lens and has a diameter of between about 0.5 mm and about 2 mm.

14. The motility analysis system of claim 13, wherein the micro lens is fabricated from H-ZLaF71, LaSFN9, or S-LAH79.

15. The motility analysis system of claim 9, wherein the sample chamber has a depth of between about 5 μm and about 20 μm.

16. The motility analysis system of claim 9, wherein the first component or second component is fabricated from soda lime glass, borosilicate glass, fused silica, cyclic olefin copolymer (COC), cyclic olefin polymer (COP), acrylic, Tyril™ 867E styrene and acrylonitrile (SAN) resin, or any combination thereof.

17. The motility analysis system of claim 9, wherein the device is a single-use disposable.

18. The motility analysis system of claim 9, wherein the light source is an LED, high intensity LED, or laser diode.

19. The motility analysis system of claim 9, wherein the light source is configured to stop functioning after a specified number of exposure cycles.

20. The motility analysis system of claim 19, wherein the specified number of exposure cycles is less than or equal to 1,000.

21. The motility analysis system of claim 9, wherein the image sensor chip is a charge-coupled device (CCD) image sensor or a complementary metal-oxide-semiconductor (CMOS) image sensor.

22. The motility analysis system of claim 9, wherein a depth-of-field of an image is between about 5 μm and about 20 μm.

23. The motility analysis system of claim 9, further comprising at least one additional lens, mirror, dichroic reflector, prism, optical filter, optical fiber, aperture, light source, image sensor chip, or any combination thereof.

24. The motility analysis system of claim 9, wherein the series of one or more image(s) acquired by the image sensor chip comprises video data.

25. The motility analysis system of claim 9, wherein the initial processing of image data comprises applying a contrast adjustment algorithm, a noise reduction algorithm, a flat-field or vignetting correction algorithm, an optical distortion correction algorithm, an optical aberration correction algorithm, a data compression algorithm, or any combination thereof to the series of one or more image(s).

26. The motility analysis system of claim 9, wherein the image sensor chip and processor are provided by a smart phone, and wherein the housing comprises a third alignment feature or adjustable fixture that facilitates optical alignment of the image sensor chip of the smart phone with the micro lens, sample chamber, and light source.

27. The motility analysis system of claim 26, wherein image acquisition by the image sensor chip is controlled by a software application running on the smart phone, and wherein the software application performs further processing of the image data that comprises performing an edge detection algorithm, an image segmentation algorithm, a centroid calculation algorithm, a feature detection algorithm, a pattern detection algorithm, a motion tracking algorithm, a mathematical analysis algorithm, a statistical analysis algorithm, or any combination thereof.

28. The motility analysis system of claim 27, wherein the further processing of the image data provides a test result for total sperm count, total sperm concentration, motile sperm count, motile sperm concentration, average sperm motility or velocity, sperm motility or velocity for the motile fraction, sperm morphology, presence of sperm morphological defects, number of sperm morphological defects, or any combination thereof.

29. The motility analysis system of claim 27, wherein the software application is configured to upload image data or a test result to a cloud-based database, and wherein all or a portion of the image processing is performed in the cloud using a cloud-based image processing algorithm.

30. The motility analysis system of claim 28, wherein one or more test results stored locally or stored in a cloud-based database are used to make an agricultural diagnostic decision, to make a clinical diagnostic decision, to guide a therapeutic decision, to monitor a therapeutic treatment regimen, or to make a marketing decision.

* * * * *